(12) United States Patent
Ries et al.

(10) Patent No.: US 8,190,260 B2
(45) Date of Patent: May 29, 2012

(54) LEAD RETENTION AND SEALING DEVICE

(75) Inventors: Andrew J. Ries, Lino Lakes, MN (US);
Eric J. Wengreen, Blaine, MN (US);
Michael R. Klardie, Bloomington, MN (US); Jennifer J. Zhao, Plymouth, MN (US); Richard A. Bruchmann, Andover, MN (US); Kathleen P. Macke, Hugo, MN (US); John E. Lovins, Oakdale, MN (US); Randy S. Roles, Elk River, MN (US)

(73) Assignee: Medtronic, Inc., Minneapolis, MN (US)

( * ) Notice: Subject to any disclaimer, the term of this patent is extended or adjusted under 35 U.S.C. 154(b) by 265 days.

(21) Appl. No.: 12/410,124

(22) Filed: Mar. 24, 2009

(65) Prior Publication Data
US 2010/0249869 A1 Sep. 30, 2010

(51) Int. Cl.
*A61N 1/375* (2006.01)
(52) U.S. Cl. .......................................................... 607/37
(58) Field of Classification Search ............... 607/36–38
See application file for complete search history.

(56) References Cited

U.S. PATENT DOCUMENTS

| | | | |
|---|---|---|---|
| 1,674,258 A | 6/1928 | Obergfell | |
| 3,592,100 A | 7/1971 | Mackiewicz et al. | |
| 4,141,752 A | 2/1979 | Shipko | |
| 4,262,673 A | 4/1981 | Kinney et al. | |
| 4,316,471 A | 2/1982 | Shipko et al. | |
| 4,479,489 A | 10/1984 | Tucci | |
| 4,907,592 A | 3/1990 | Harper | |
| 4,934,366 A | 6/1990 | Truex et al. | |
| 5,413,595 A | 5/1995 | Stutz, Jr. | |
| 5,509,928 A * | 4/1996 | Acken | 607/37 |
| 5,522,861 A | 6/1996 | Sikorski et al. | |
| 5,626,626 A | 5/1997 | Carson | |
| 5,679,026 A | 10/1997 | Fain et al. | |
| 5,683,433 A | 11/1997 | Carson | |
| 5,899,930 A | 5/1999 | Flynn et al. | |
| 5,913,881 A | 6/1999 | Benz et al. | |
| 6,044,302 A | 3/2000 | Persuitti et al. | |
| 6,112,120 A | 8/2000 | Correas | |
| 6,112,121 A | 8/2000 | Paul et al. | |
| 6,205,358 B1 | 3/2001 | Haeg et al. | |
| 6,609,029 B1 | 8/2003 | Mann et al. | |
| 6,643,550 B2 | 11/2003 | Westlund et al. | |
| 6,862,478 B1 | 3/2005 | Goldstein | |
| 6,879,857 B2 | 4/2005 | Swanson et al. | |

(Continued)

FOREIGN PATENT DOCUMENTS

DE 19710960 9/1998

(Continued)

*Primary Examiner* — Carl H Layno
*Assistant Examiner* — Roland Dinga
(74) *Attorney, Agent, or Firm* — Scott A. Bardell; Stephen W. Bauer; Evans M. Mburu

(57) ABSTRACT

This application discusses, among other things, a header assembly for coupling a medical electrical lead to a medical stimulating device including a header having a capture mechanism within a bore of a lead retention device. In an example, when the lead retention device is retracted from the bore, the capture mechanism prevents the device from falling out. In another example, the header assembly has a vent disposed within the bore of the lead retention device that permits unrestricted flow of air when the lead retention device is retracted from an engagement surface.

4 Claims, 24 Drawing Sheets

U.S. PATENT DOCUMENTS

| | | |
|---|---|---|
| 6,912,423 B2 | 6/2005 | Ley et al. |
| 7,017,077 B2 | 3/2006 | Lowen et al. |
| 7,069,081 B2 | 6/2006 | Biggs et al. |
| 7,155,283 B2 | 12/2006 | Ries et al. |
| 7,167,749 B2 | 1/2007 | Biggs et al. |
| 7,174,211 B2 | 2/2007 | Spadgenske |
| 7,187,975 B2 | 3/2007 | Flickinger et al. |
| 7,210,968 B1 | 5/2007 | Gister et al. |
| 7,231,253 B2 | 6/2007 | Tidemand et al. |
| 7,274,964 B2 | 9/2007 | Balsells |
| 7,308,312 B1 | 12/2007 | Lim et al. |
| 7,308,313 B1 | 12/2007 | Lim et al. |
| 2002/0107555 A1 | 8/2002 | Rusin et al. |
| 2004/0093038 A1 | 5/2004 | Biggs et al. |
| 2004/0225334 A1 | 11/2004 | Persuitti et al. |
| 2005/0131481 A1 | 6/2005 | Ries et al. |
| 2005/0131483 A1 | 6/2005 | Zhao et al. |
| 2006/0247716 A1* | 11/2006 | Fruland et al. .................. 607/36 |
| 2006/0259092 A1 | 11/2006 | Spadgenske et al. |
| 2007/0049985 A1 | 3/2007 | Kessler et al. |
| 2007/0225772 A1 | 9/2007 | Lahti et al. |
| 2008/0009912 A1 | 1/2008 | Spadgenske |
| 2008/0077190 A1 | 3/2008 | Kane et al. |

FOREIGN PATENT DOCUMENTS

| | | |
|---|---|---|
| JP | 1999006511 | 1/1999 |
| JP | 2003113821 | 4/2003 |

* cited by examiner

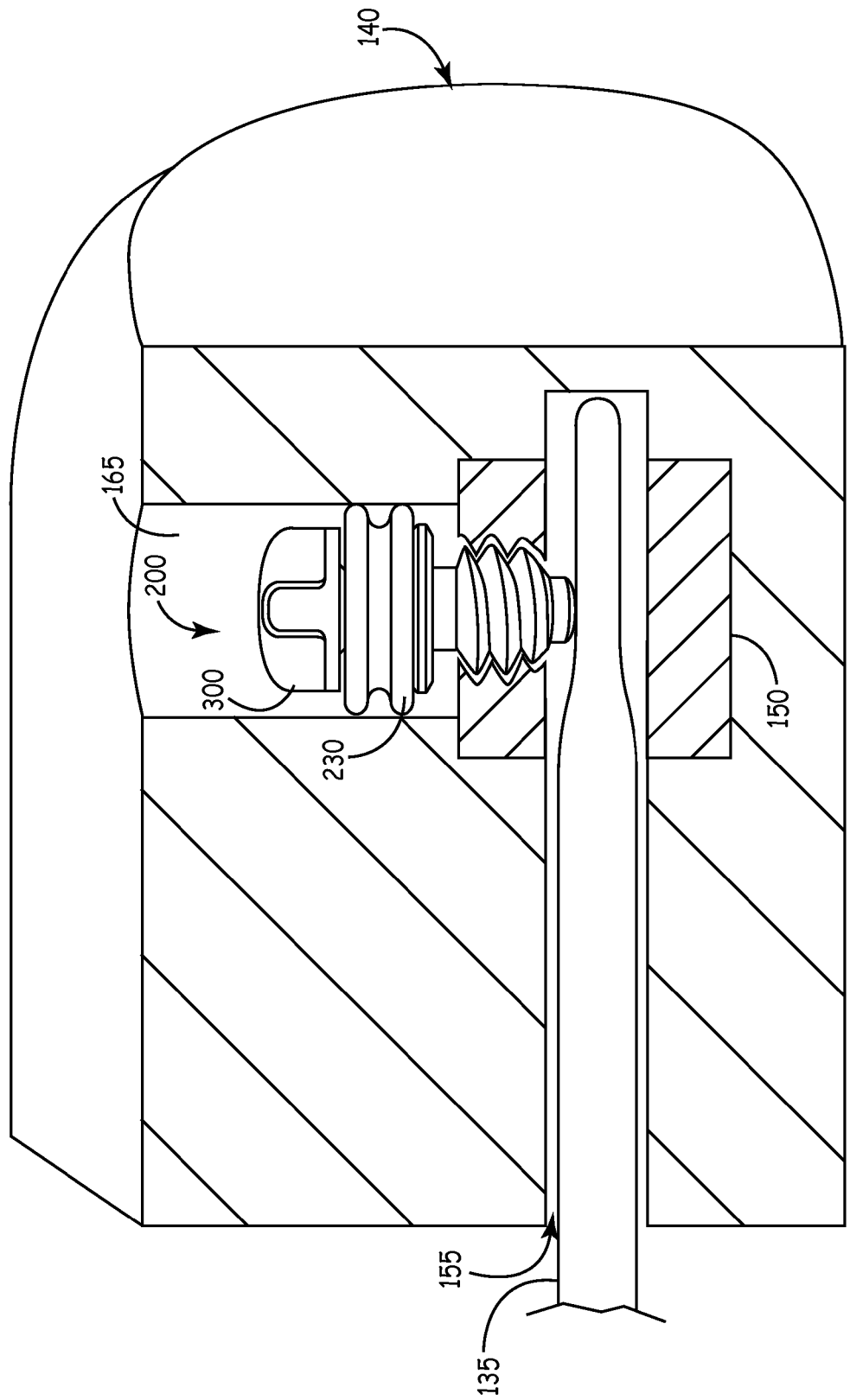

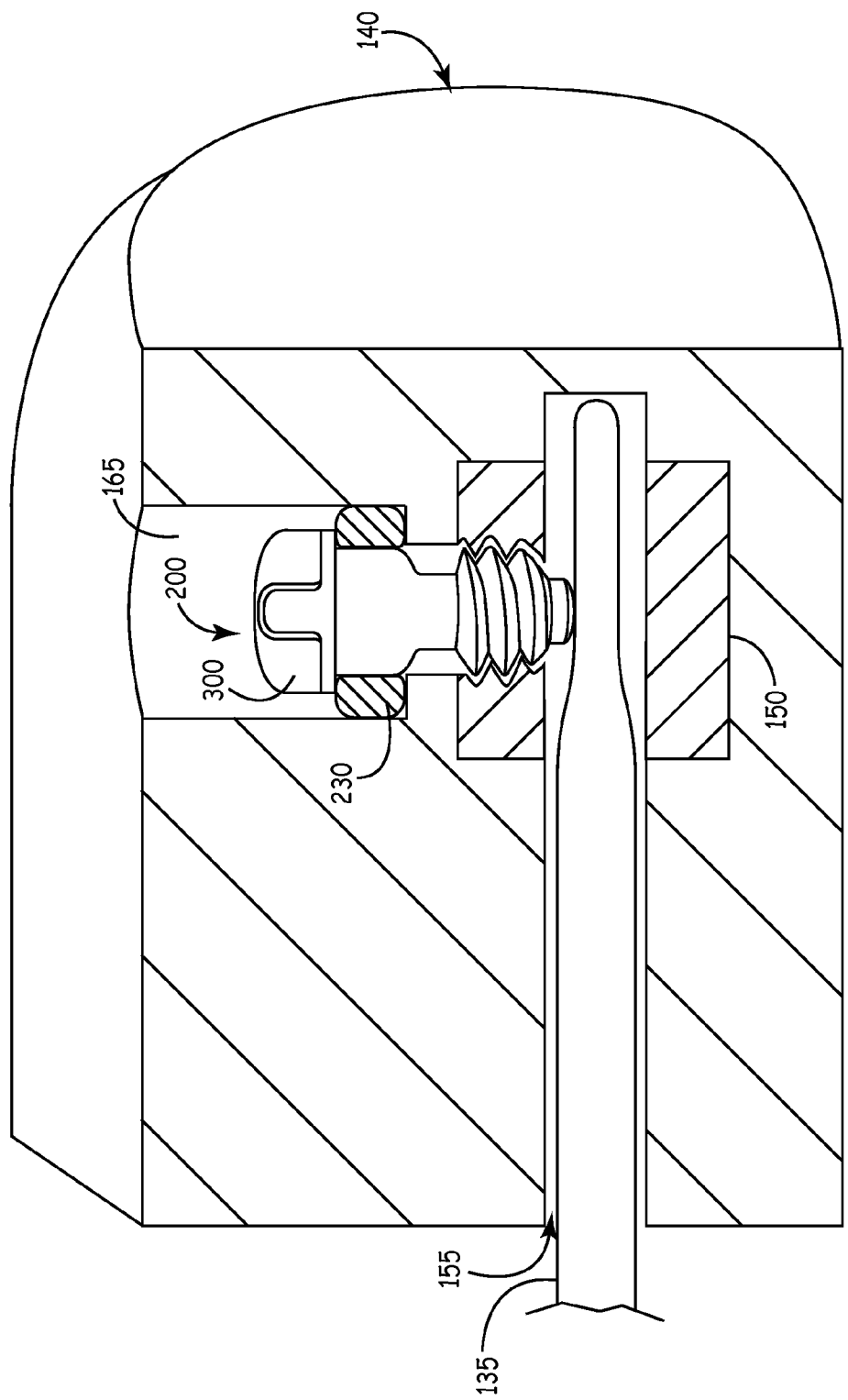

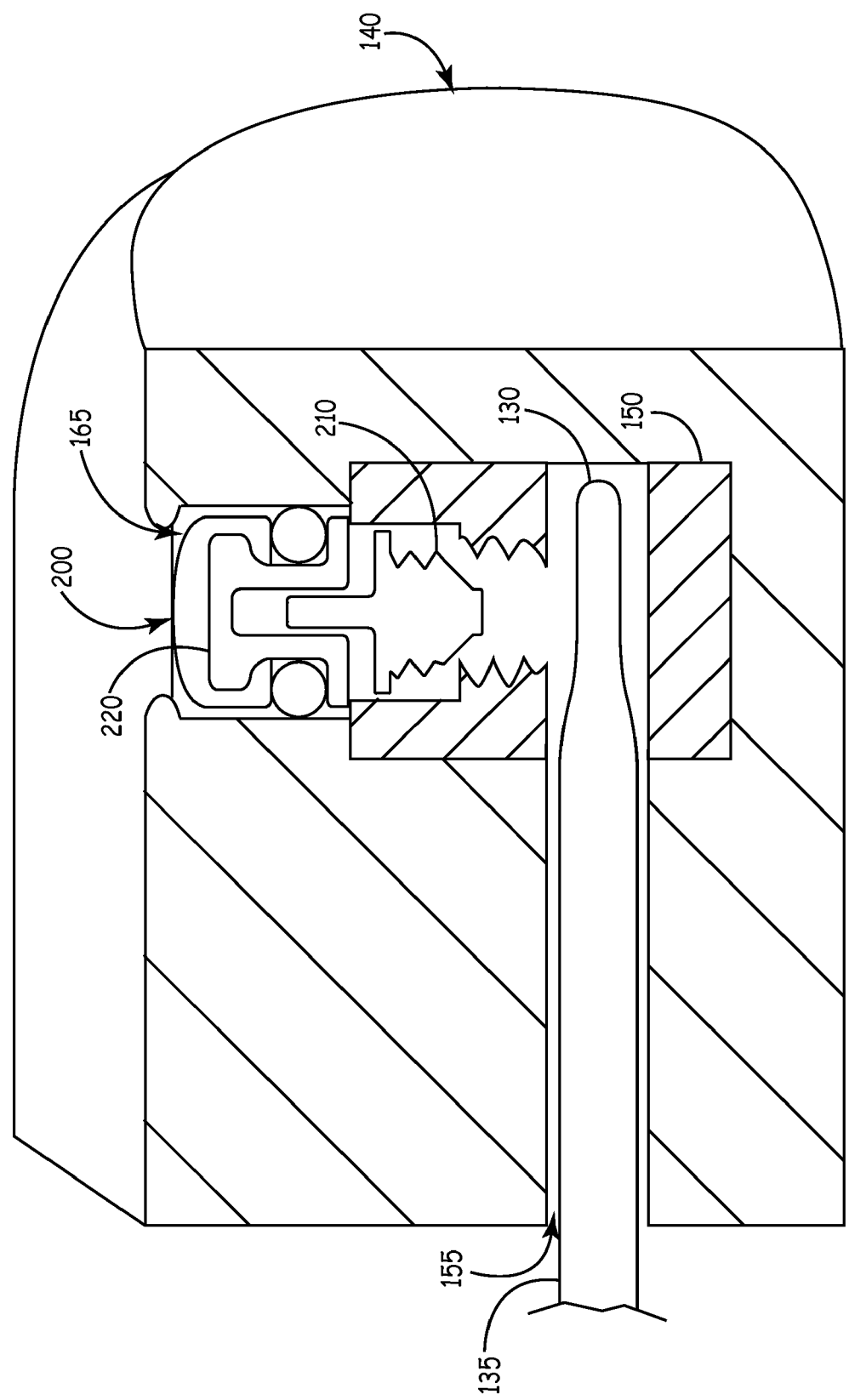

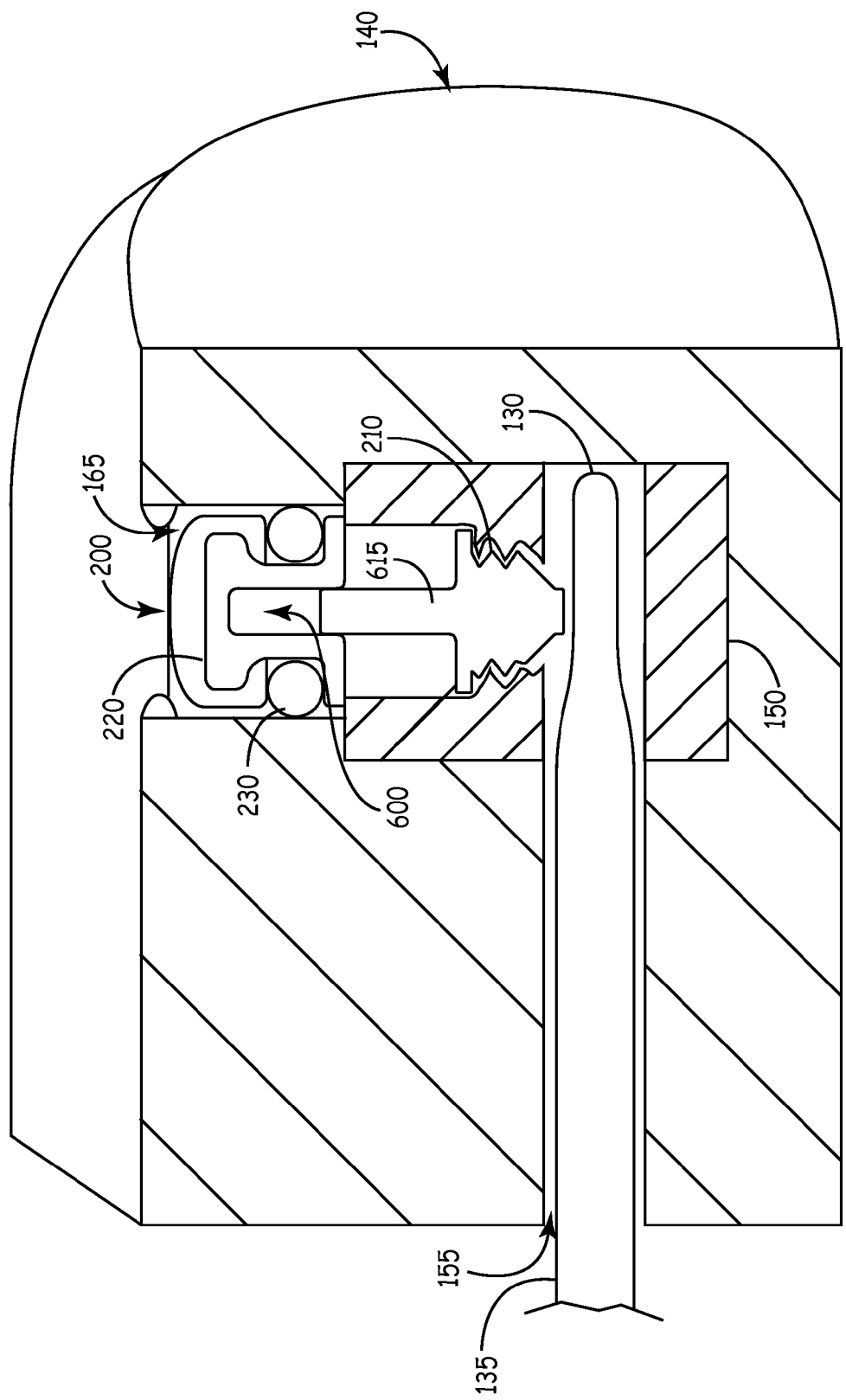

LEAD RETENTION AND SEALING DEVICE

CROSS REFERENCE TO RELATED APPLICATIONS

Reference is made to commonly-assigned and co-pending application U.S. Ser. No. 12/410,233, filed Mar. 24, 2009, entitled "Full Visibility Lead Retention;" and U.S. Ser. No. 12/410,203, filed Mar. 24, 2009, entitled "Lead Retention and Sealing Device," all of which are herein incorporated by reference in their entirety.

TECHNICAL FIELD

The present disclosure generally relates to implantable medical devices. More specifically and without limitation, this disclosure relates to headers and setscrews for implantable medical devices.

BACKGROUND

Many implantable medical devices such as pacemakers, defibrillators and neural stimulators deliver electrical therapy to tissue and sense various physiological parameters via medical leads. Such leads typically include an elongated flexible lead body with one or more electrodes disposed at a distal end of the lead. The electrodes are connected to a terminal pin on the lead's proximal end by conductors that are disposed within the lead body.

The lead is typically coupled to a header of the implantable medical device with a proximal portion of the lead being secured within the header to prevent the lead from dislodging. In general, the header has a connector block that includes a lead bore into which the lead's proximal portion is received. The connector block also includes a threaded setscrew bore that intersects with the lead bore. The setscrew bore receives a setscrew that engages the lead to secure it within the header.

The connector block is also coupled to a feedthrough pin, which passes through hermetic seals to connect with input and/or output nodes of the implantable medical device's electronic circuitry. Typically, the connector block is formed from a conductive material, such as metal, thereby permitting electrical connectivity between the lead and the electronic circuit.

To provide a reliable connection of the lead within the connector block, the setscrew is typically comprised of metal. Thus, the contact with the electrically active connector block causes the setscrew to be electrically active. Exposure of the setscrew to adjacent body tissue and body fluids might result in undesired electrical conduction to the adjacent tissue. Additionally, because the setscrew bore intersects with the terminal pin of the lead, ingress of fluid into the setscrew bore may result in the fluid contacting the terminal pin and this may compromise the device's delivery of electrical therapy. Consequently, a septum, typically referred to as a grommet, is disposed within the setscrew bore to cover the setscrew, thereby sealing the setscrew bore and isolating the electrically active setscrew from body fluids. In one example, the grommet is a silicone disk that has an elastic quality and has a slit that allows passage of a screw driver for tightening the setscrew and re-seals upon removal of the torque wrench to block entry of body fluids. Additionally, when the shank of the setscrew is disengaged from the threaded bore, the grommet retains the setscrew and prevents it from falling out.

While the use of a grommet has been satisfactory at preventing entry of fluids into the device and contact between the electrically active setscrew and surrounding tissue, it also substantially obstructs the visibility of the lead's terminal pin within the connector block. Lead tip visibility is an indicator of full lead insertion into the conductive block. The visibility enables verification that a proper and secure electrical and mechanical connection between the lead and the conductive block has been made.

BRIEF SUMMARY

Embodiments of the present disclosure provide, among other things, a setscrew that enables lead tip visibility as an indicator of full lead insertion without requiring a grommet. In one embodiment, a setscrew is provided having a metal core with an insulative coating disposed over the core to electrically isolate it from body fluids and surrounding tissue without requiring a grommet. In one embodiment, the setscrew incorporates a sealing capability by including a sealing member that is coupled to the setscrew. In another embodiment, the sealing member is disposed within the setscrew bore to engage the setscrew. The sealing capability seals the setscrew bore to prevent entry of body fluids into the implantable medical device.

In one embodiment, the setscrew is provided with an engagement segment on a head portion that is configured for engagement with a torque wrench. In another embodiment, a reinforcement sleeve is disposed on the setscrew head. In one example, the reinforcement sleeve is disposed on the entire head. In another example, the reinforcement sleeve is disposed on the engagement segment of the head.

In another embodiment, an implantable medical device header has a setscrew bore configured for engagement with a setscrew. The setscrew bore is provided with an undercut that is formed at a location proximate to the exterior opening of the setscrew bore.

In another embodiment, the setscrew bore has a capture mechanism that at least partially covers the exterior opening of the setscrew bore. Thus, when the setscrew is retracted from the threaded region of the bore, the capture mechanism prevents the setscrew from falling out. In some embodiments, the capture mechanism has a radial opening having a diameter that is less than the diameter of the setscrew while still allowing insertion of a torque inducing tool.

In another embodiment, an implantable medical device header is provided with a lead bore and a setscrew bore with the setscrew bore having a longitudinal axis that extends in a transverse direction to, and in communication with, the lead bore. In one example, the setscrew bore intersects with the lead bore at a location that is offset from the central longitudinal axis of the lead bore.

BRIEF DESCRIPTION OF THE DRAWINGS

The following drawings are illustrative of particular embodiments of the present disclosure and therefore do not limit the scope of the disclosure. The drawings (not to scale) are intended for use in conjunction with the explanations in the following detailed description, wherein similar elements are designated by identical reference numerals. Moreover, the specific location of the various features is merely exemplary unless noted otherwise.

FIG. 2A shows a perspective view of a cut-out of the header of FIG. 1 taken along lines 2-2;

FIG. 2B shows a perspective view of an alternative embodiment of the header of FIG. 1 taken along lines 2-2;

FIG. 9A-B illustrate cross-sectional views of header 140 in conjunction with setscrew 200 of FIG. 8;

DETAILED DESCRIPTION

The following description is exemplary in nature and is not intended to limit the scope, applicability, or configuration of the present disclosure in any way. Rather, the description provides practical illustrations for implementing exemplary embodiments of the present disclosure.

Figure 1:
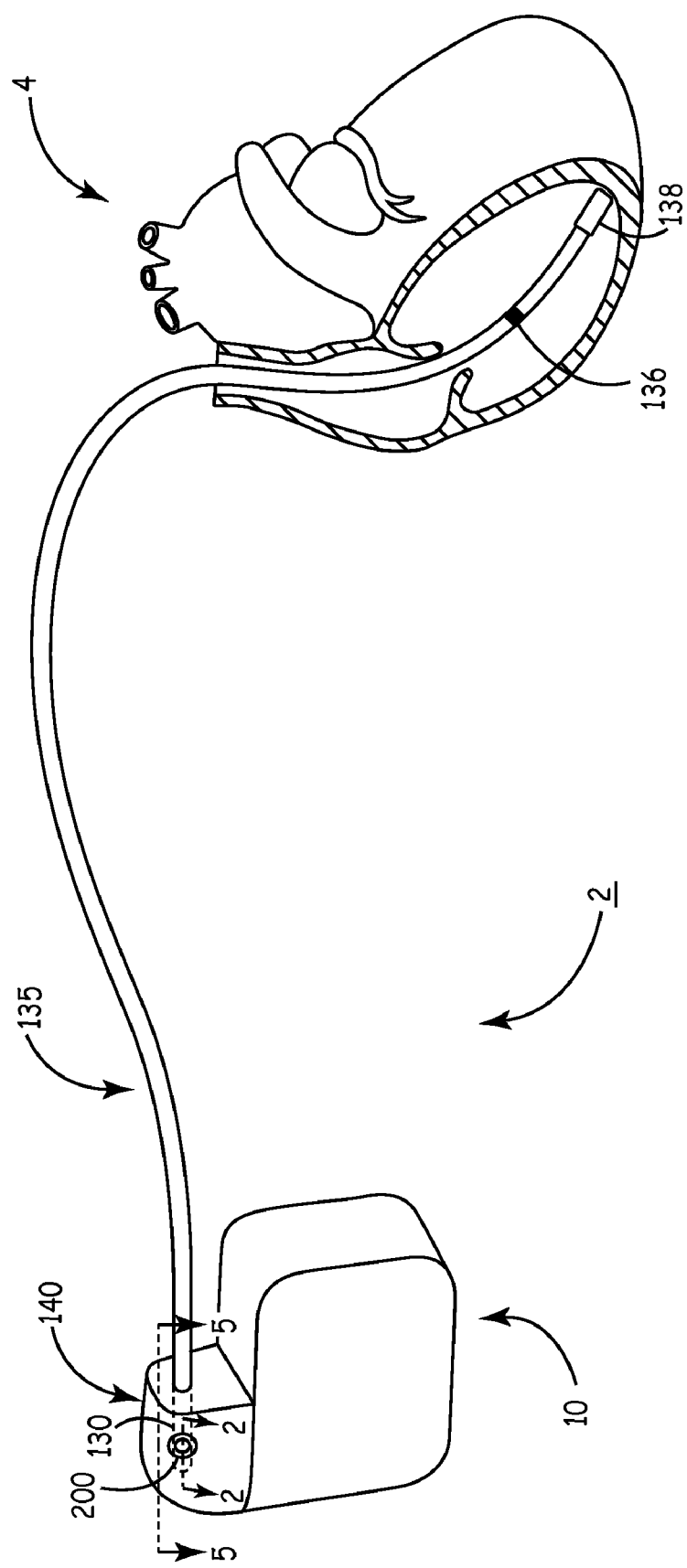
FIG. 1 is an illustration of an example implantable medical device system that has a lead extending into a heart.

FIG. 1 is an illustration of an example implantable medical device system 2 including an implantable medical device (IMD) lead 135 connected to an IMD 10. In some embodiments, IMD 10 takes the form of a cardiac pacemaker, defibrillator, neurostimulator, muscle stimulator, or gastric stimulator. As will be described in more detail below, the proximal end of lead 135 is coupled to a header 140 of IMD 10. Lead 135 is secured in header 140 by a setscrew 200, which will be described in more detail below. A distal end of lead 135 is coupled to an organ or any other desired tissue such as, for example, a heart 4. IMD 10 delivers electrical stimulation to the tissue and/or detects electrical activity via electrodes 136, 138. The illustration of the embodiment of FIG. 1 showing IMD 10 coupled to a single lead 135 is merely for ease of description of the various aspects of the present disclosure and is not intended to be limiting. For example, in one or more embodiments, IMD 10 is coupled to a plurality of leads 135.

FIG. 2A is an isovolumetric sectional view of header 140 taken along lines 2-2 (FIG. 1). Header 140 includes a connector block 150 comprised of a suitable biocompatible material that is also electrically conductive such as titanium. Connector block 150 includes a lead bore 155 into which lead 135 is received. Connector block 150 also includes a setscrew bore 165 which receives setscrew 200. Setscrew bore 165 is oriented to be in alignment with, and intersect, lead bore 155. In other words, the central longitudinal axis of setscrew bore 165 is oriented in a transverse direction, relative to the longitudinal axis of lead bore 155. Therefore, when setscrew 200 is threaded into setscrew bore 165, a distal tip 290 abuts lead 135 thereby securing it within header 140.

Setscrew 200 has a tool interface 300 that has a generally cross-shaped external drive interface. An external drive interface, generally, has faces that are aligned with the thread axis and face outward. Tool interface 300 facilitates the threading of setscrew 200 into the setscrew bore 165.

A sealing member 230 is coupled to setscrew 200. The engagement of sealing member 230 between setscrew 200 and setscrew bore 165 seals the region of header 140 extending inwardly of sealing member 230 to prevent penetration of body fluids. Sealing member 230 can be any component that forms a fluid seal such as an o-ring or wiper seal. In some embodiments, the material used to form the seal is silicone.

FIG. 2B illustrates an alternative embodiment of the header 140 of FIG. 2A incorporating sealing member 230 onto setscrew bore 165. Thus, sealing member 230 is circumferentially disposed within setscrew bore 165. In some embodiments, engagement of setscrew 200 compresses sealing member 230 against setscrew bore 165 or connector block 150 to form a seal.

Figure 3:
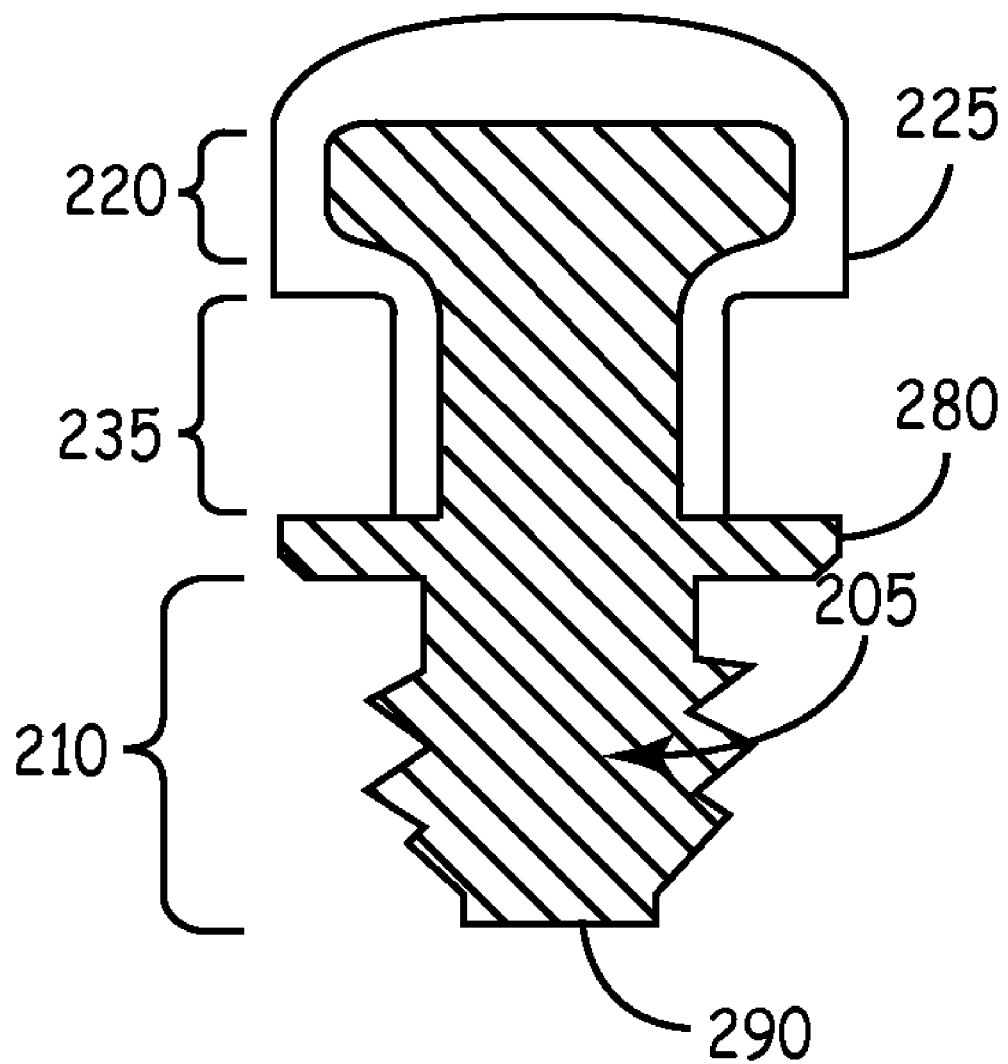
FIG. 3 is a cross-sectional view of one embodiment of setscrew 200.

FIG. 3 is a cross-sectional view of one embodiment of setscrew 200. Setscrew 200 includes a core 205 having a head portion 220 and a threaded shank portion 210. Shank 210 has a thread type compatible with a threaded setscrew bore 165 such, for example, as a standard 2-56 UNC-2A screw thread. In one embodiment, core 205 also includes a necked region 235. Necked region 235 is formed between head portion 220 and shank 210 and has a narrower diameter than head 220. In some embodiments, the sealing member 230 is coupled to necked region 235. Core 205 includes a shoulder 280 disposed between necked region 235 and shank 210. Shoulder 280 is dimensioned to limit the downward movement of setscrew 200 by abutting connector block 150 (FIG. 2A). In the illustrative embodiment of FIG. 3, head portion 220 and shank 210 are integrally formed to define unitary core 205. In some embodiments, core 205 is comprised of a material having a high resiliency and strain endurance with the ability to be deformed under stress without cleaving such, for example, as a metal, organic metals or metallic polymers. In other embodiments, the material is a suitable biocompatible material and or is electrically conductive such, for example, as gold, titanium or their alloys. In other embodiments, core 205 does not significantly deform under typical loading conditions such as the forces exerted during the assembly process.

Setscrew 200 includes insulating coating 225 that is disposed over a portion of core 205. In the illustrative embodiment, insulating coating 225 is disposed over head 220 and necked region 235. Insulating coating 225 will prevent exposure of surrounding tissue or fluids to electrical current generated by IMD 10 (FIG. 1) and will prevent exposure of the lead 135 to the electrical signals of the tissue outside the header. Insulating coating 225 is generally a non-conductive material that has dielectric properties. In one example, the material selected for insulating coating 225 is a biocompatible dielectric material such as polyaryletheretherketone (PEEK) thermoplastic, PARYLENE® polyxylylene polymers, or a suitable polymer material. Insulating coating 225 is coupled to core 205 by any conventional coating, molding or deposition processes. Insulating coating 225 is applied in a thickness to prevent electrical conduction via core 205 that may arise from contact with the electrically active connector block 150. In an example where insulating coating 225 is primarily relied upon to provide electrical insulation from the surrounding medium, the thickness of insulating coating 225 is typically in the range of about 0.1 mm to about 0.8 mm (0.0039 inches to 0.0315 inches). However, the thickness of insulative coating 225 may also be determined by the thickness necessary to ensure the force from a wrench 302 (FIG. 4A) used to tighten and loosen the setscrew will not jeopardize the dielectric integrity of the insulator by tearing, cracking, penetrating, or otherwise weakening the insulative coating 225.

Figures 4A, 4B:
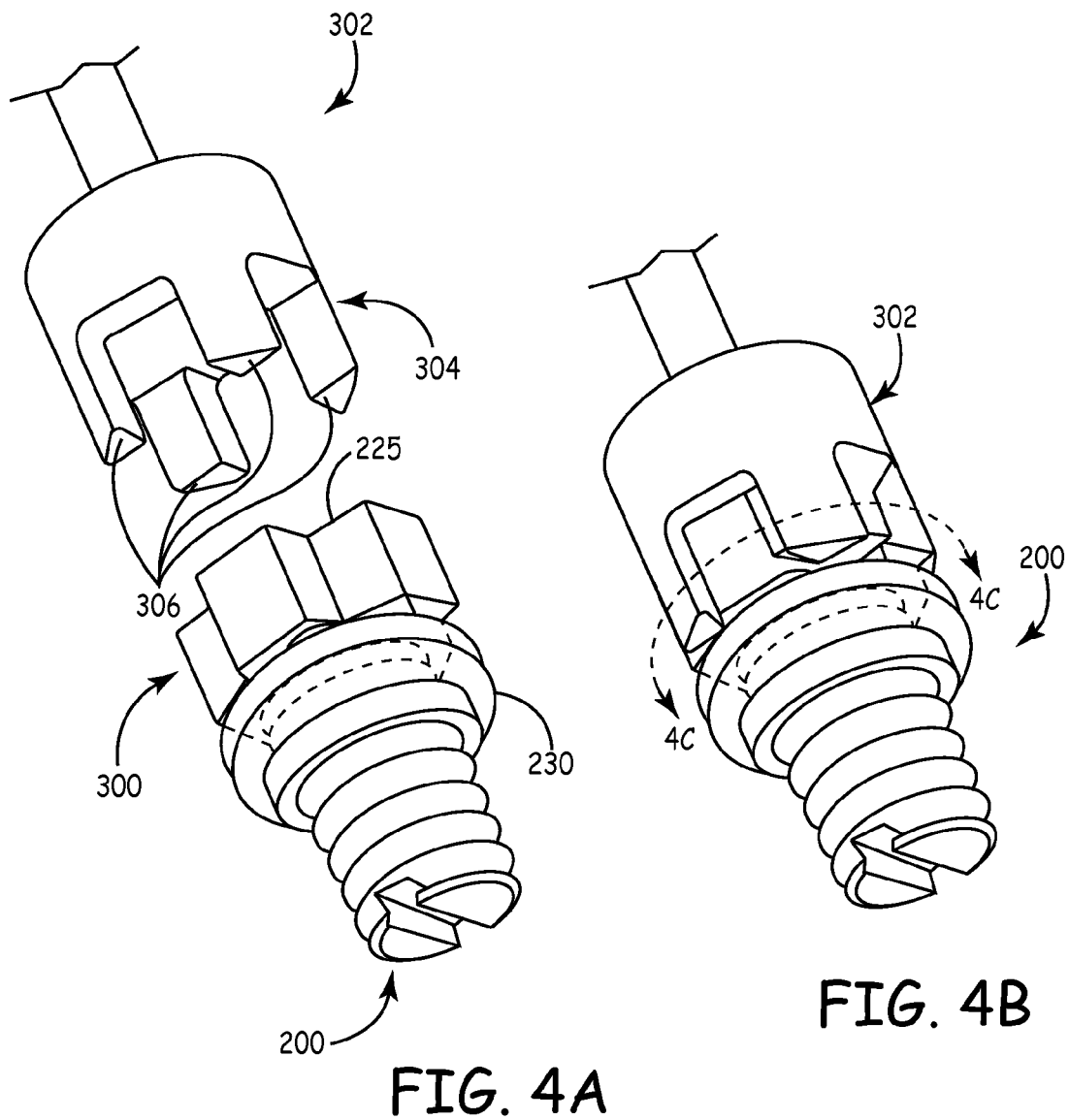
FIGS. 4A-C illustrate perspective views of the coupling between a torque wrench and a setscrew of the present disclosure.
Figure 4C:
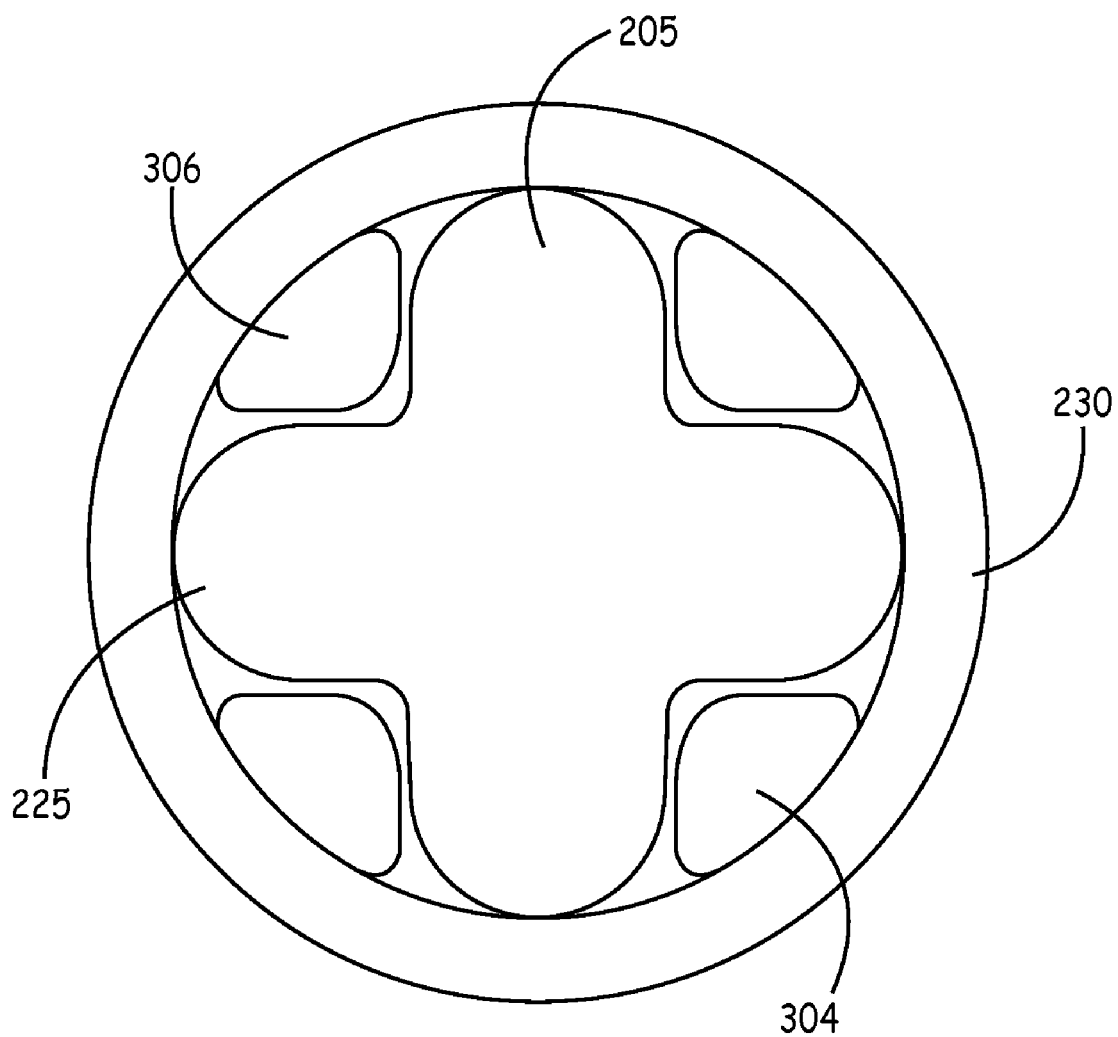

FIGS. 4A-C illustrate the coupling between torque wrench 302 and setscrew 200. As shown in the exemplary embodiment of FIG. 4A, tool interface 300 is configured such that it interfaces with mating segment 304 of torque wrench 302. The apex of tool interface 300 may be configured to be a guiding surface such that it facilitates the positioning of torque wrench 302 over the setscrew 200. As an example, the apex of tool interface 300 is formed as a dome-shape. As illustrated in FIG. 4B mating segment 304 fits over tool interface 300, in direct contact with insulating coating 225. Thus, torque applied by torque wrench 302 is transferred to both insulating coating 225 and tool interface 300. Due to insulating coating 225 being trapped between torque wrench 302 and core 205, the torque motion compresses insulating coating 225 against core 205. Accordingly, insulating coating 225 is placed primarily under compressive stress, rather than shear stress. The underlying core 205 provides a high rigidity to insulating coating 225, which is placed primarily in compression, thereby increasing the torque bearing capability of setscrew 200.

FIG. 4C illustrates a cross sectional view of the coupling of setscrew 200 to torque wrench 302. Prongs 306 of mating segment 304 fit in between the tool interface 300 walls. Thus, the torque motion exerted by wrench 302 places insulating coating 225 in compression against core 205.

Figure 5:
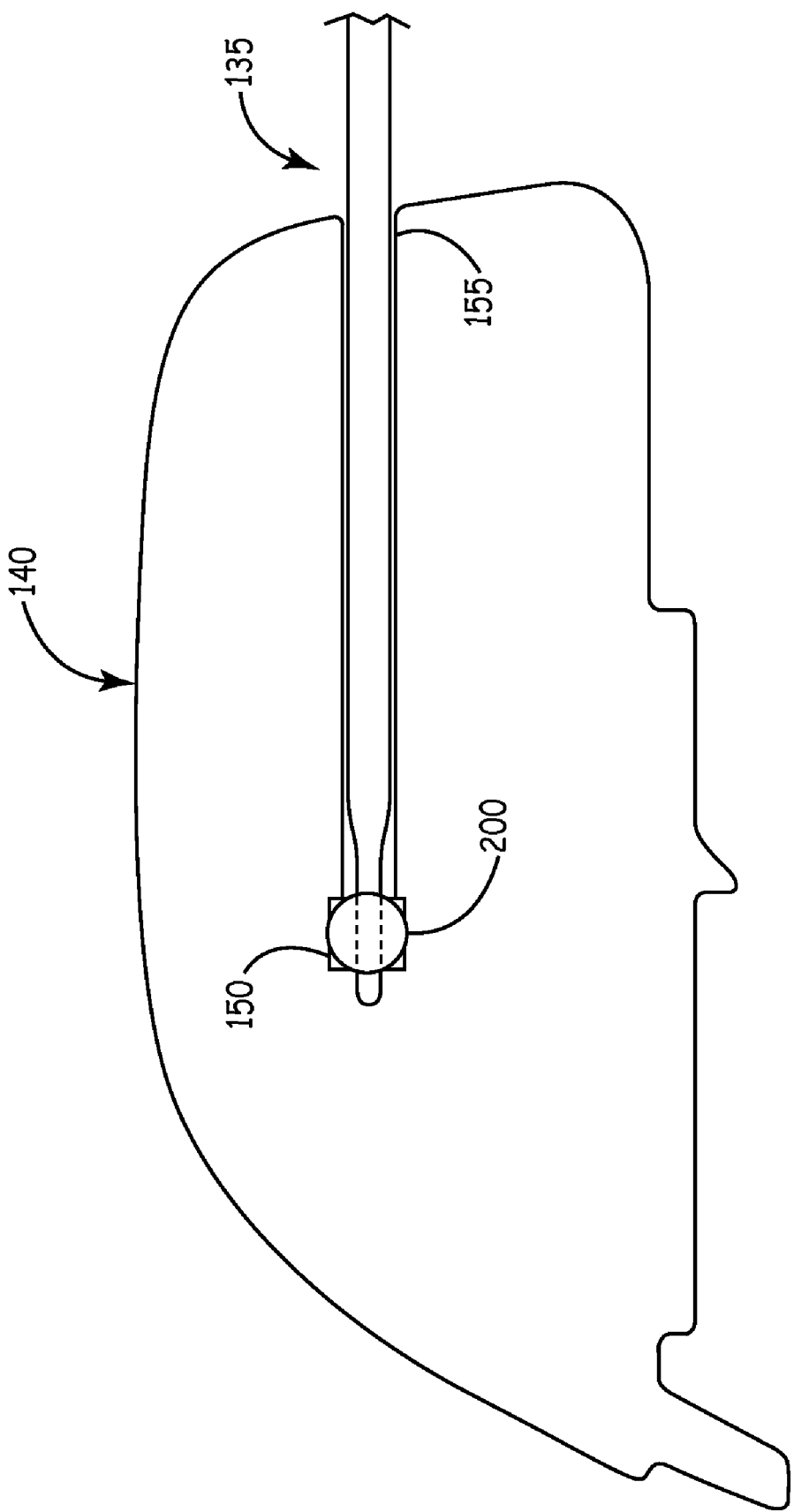
FIG. 5 shows a cross sectional view of header 140 taken along lines 5-5 (FIG. 1)

With reference to FIG. 5, a cross sectional view of header 140 taken along lines 5-5 of FIG. 1 is illustrated. Lead 135 and setscrew 200 are insertable into connector block 150 as described above. As the view illustrates, lead 135 is engaged within connector block 150 thereby providing the physical contact for electrical connectivity of lead 135 with the electrical circuit (not shown) of IMD 10. The engagement of lead 135 with connector block 150 provides the electrical connectivity with the electrical circuit. The overall diameter arising from the implementation of setscrew 200 with a core 205 facilitates the visibility of the engagement between lead 135 and connector block 150. Accordingly, the engagement of lead 135 with connector block 150 can be verified visually based on the protrusion of lead 135 from the connector block 150.

Figure 6A:
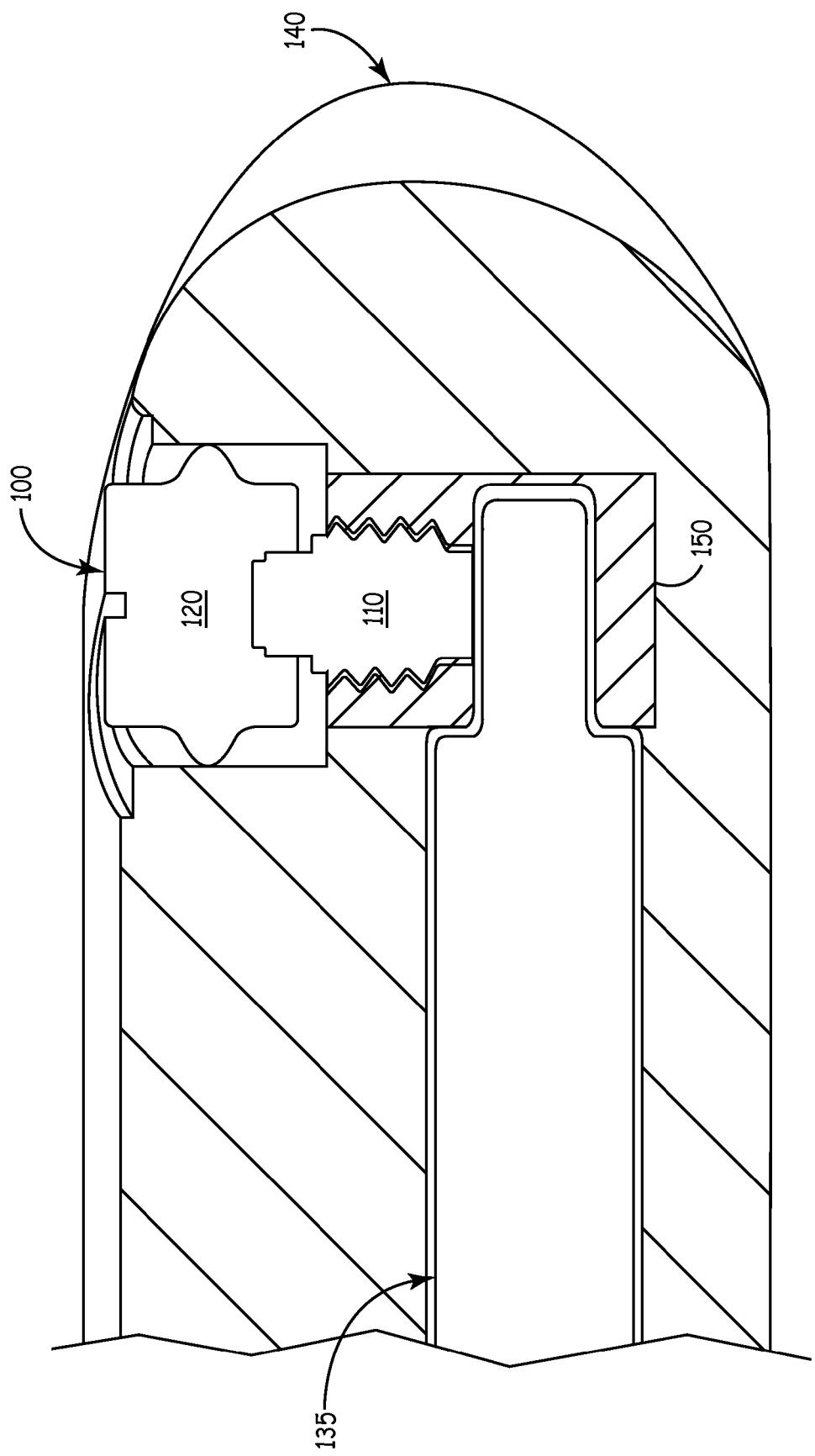
FIGS. 6A-B illustrate cross sectional views of header 140 in conjunction with a prior art setscrew.
Figure 6B:
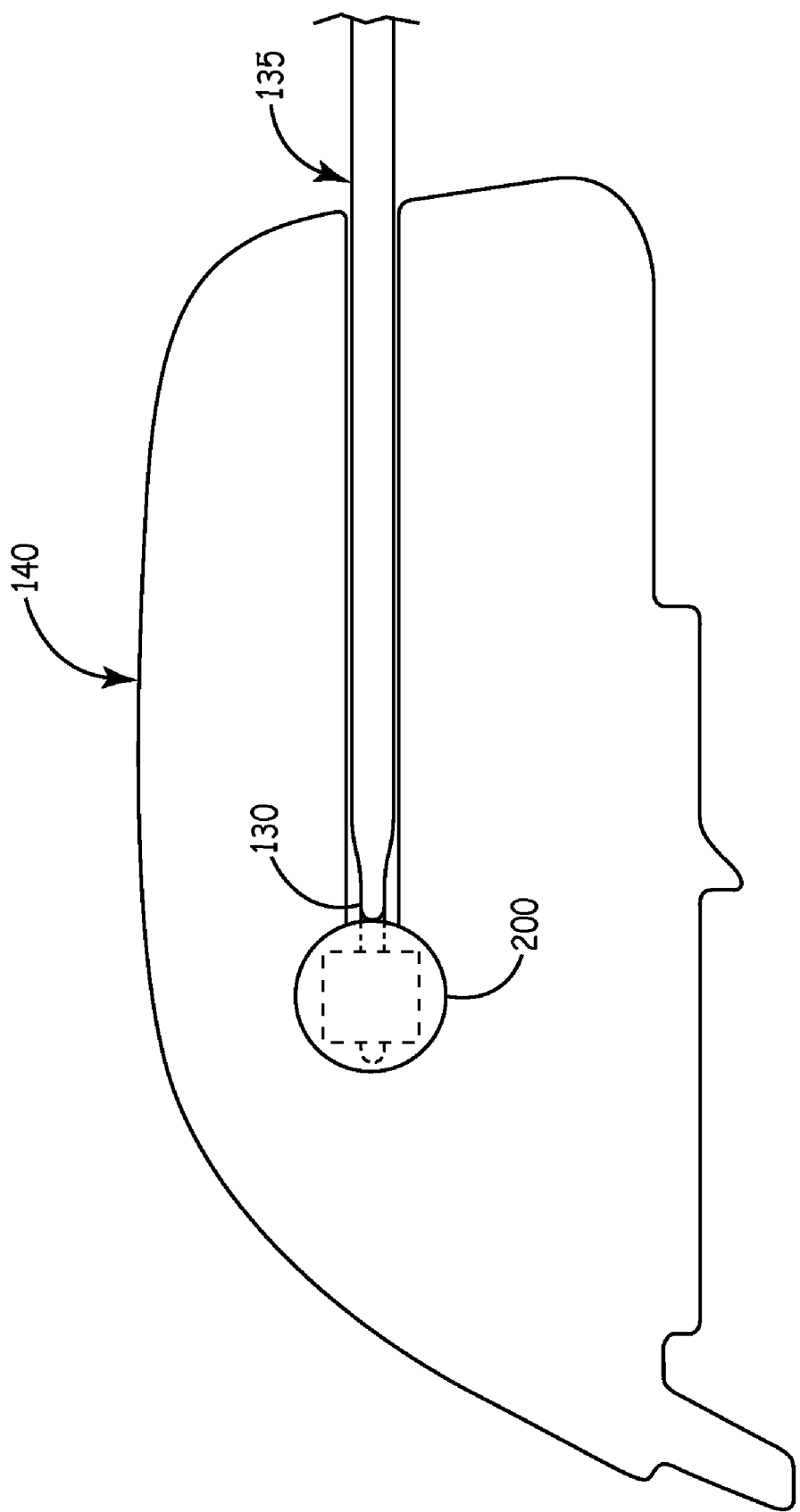

FIGS. 6A-B illustrate cross sectional views of assemblies of header 140 with a prior art setscrew 100. FIG. 6A is a side cross sectional view (similar to lines 1-1 of FIG. 1) showing lead 135 and a prior art setscrew 100, such as that disclosed in U.S. Pat. No. 4,316,471 issued to Shipko et al., inserted into connector block 150. Setscrew 100 includes a plastic head 120 that is coupled to a threaded metal shaft member 110. Torque applied to head 120 is transferred to shaft member 110 to threadedly engage setscrew 100 within header 140. The indirect transfer of torque from a screwdriver (not shown) to shaft member 110, via head 120, places head 120 under sheer stress. Due to the sheer stress loading, head 120 is formed with a large diameter to prevent tearing from the sheering stress. Thus, setscrew 100 has an overall diameter that is much larger in comparison to setscrew 200 (FIG. 3).

FIG. 6B illustrates the top cross sectional view (similar to lines 2-2 of FIG. 1) of setscrew 100 inserted into header 140. As illustrated, the large cross-sectional area of setscrew 100 obstructs visibility of connector block 150 and lead 135. As a result of the obstructed visibility, setscrew 100 inhibits visual verification of the engagement, or lack of engagement, between lead 135 and connector block 150. Therefore, visual determination of whether lead 135 is fully engaged, partially engaged, or fully disengaged from connector block 150 is prevented.

Consequently, contrasting the assembly of FIG. 5 with the assembly in FIG. 6B, setscrew 200 facilitates visibility of the engagement between lead 135 and connector block 150. As described above, due to setscrew 200 being formed with core 205 having both head portion 220 and shank 210, the overall diameter of setscrew 200 is small, relative to setscrew 100, while maintaining the same or better torque bearing ability. Moreover, while the overall volume of setscrew 200 is much smaller compared to that of setscrew 100, the engagement capability of setscrew 200 is still sufficient to prevent dislodgment of lead 135.

Figure 7:
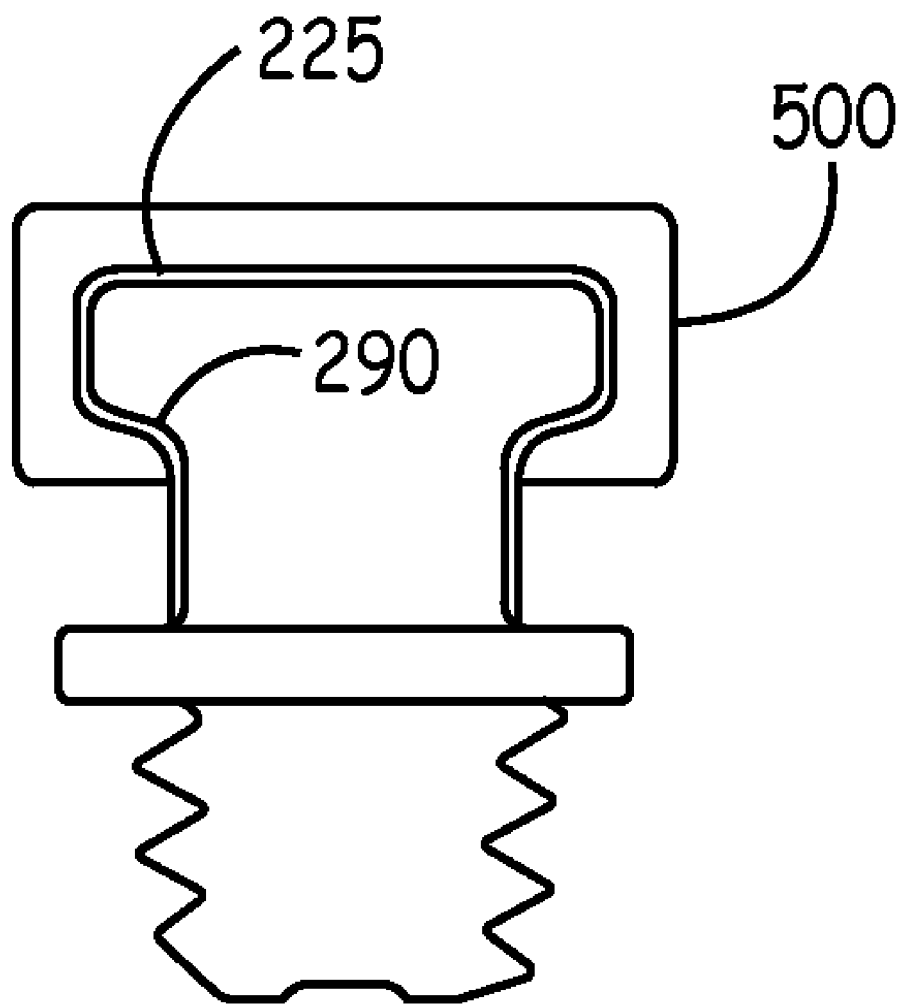
FIG. 7 illustrates an alternative embodiment of a setscrew of the present disclosure.

Turning now to FIG. 7, an alternative embodiment of setscrew 200 having a reinforcement sleeve 500 is illustrated. As described above, insulating coating 225 is contemplated to come in contact with torque wrench 302 during implantation. Depending on the thickness and/or properties of insulating coating 225, or the amount of force exerted, the contact may result in chaffing, abrasion or other physical damage that could potentially compromise the electrical insulation. Thus, reinforcement sleeve 500 is disposed over insulating coating 225 to prevent damage that may arise from improper contact between torque wrench 302 with insulating coating 225 or other mishandling of setscrew 200. Reinforcement sleeve 500 is comprised of a resilient and high strain endurance material, for example, a metal. In certain embodiments, the material is also a suitable biocompatible material, for example, gold, titanium or their alloys. In one example, the material for reinforcement sleeve 500 is an electrically insulative material that provides electrical isolation of setscrew 200. Reinforcement sleeve 500 is coupled to setscrew 200 through any suitable bonding method such, for example, as adhesion with an adhesive compound. In one embodiment, reinforcement sleeve 500 is bonded to head 220, over insulating coating 225. While not intended to be limiting, the exemplary embodiment shows reinforcement sleeve 500 enveloping a portion of head 220.

Figure 8:
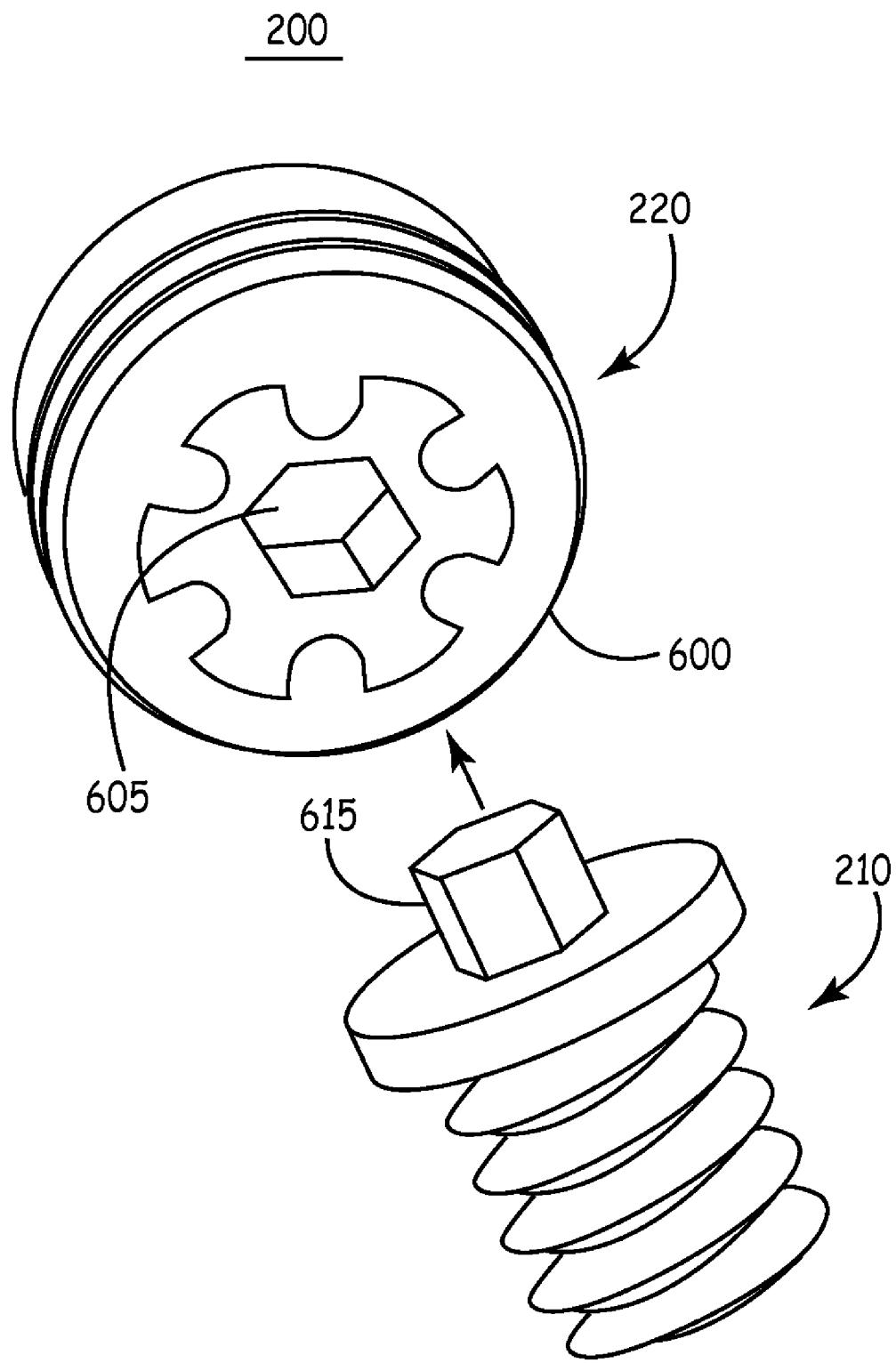
FIG. 8 illustrates another alternative embodiment of a setscrew of the present disclosure.

FIG. 8 illustrates another embodiment of setscrew 200 of the present disclosure. In this embodiment, setscrew 200 has shank 210 detachedly coupled to head 220. Head 220 includes an opening 605 that is disposed on distal end 600 into which a coupling segment 615 of shank 210 is received. In one example, opening 605 and coupling segment 615 are configured in an interlocking manner such as a lock and key arrangement such that coupling segment 615 is configured to fit into opening 605.

FIG. 9A-B illustrate cross-sectional views of header 140 in conjunction with setscrew 200 of FIG. 8. In the illustration of FIG. 9A, coupling segment 615 (FIG. 8) is fully inserted within opening 605 (FIG. 8). Head 220 is configured to be positioned at a stationary location within setscrew bore 165. As such, vertical motion of head 220 is inhibited but rotational motion is allowed. In this embodiment, when torque is applied to setscrew 200, head 220 rotates about the stationary location and the rotational movement causes vertical motion of shank 210 due to the engagement of the setscrew's threads with the connector block's threads.

As shown in FIG. 9B, rotation of head 220 causes shank 210 to be advanced into setscrew bore 165 to abut lead 135. Alternatively, head 220 can be rotated in the counter direction to retract shank 210 causing it to disengage lead 135.

Figure 10:
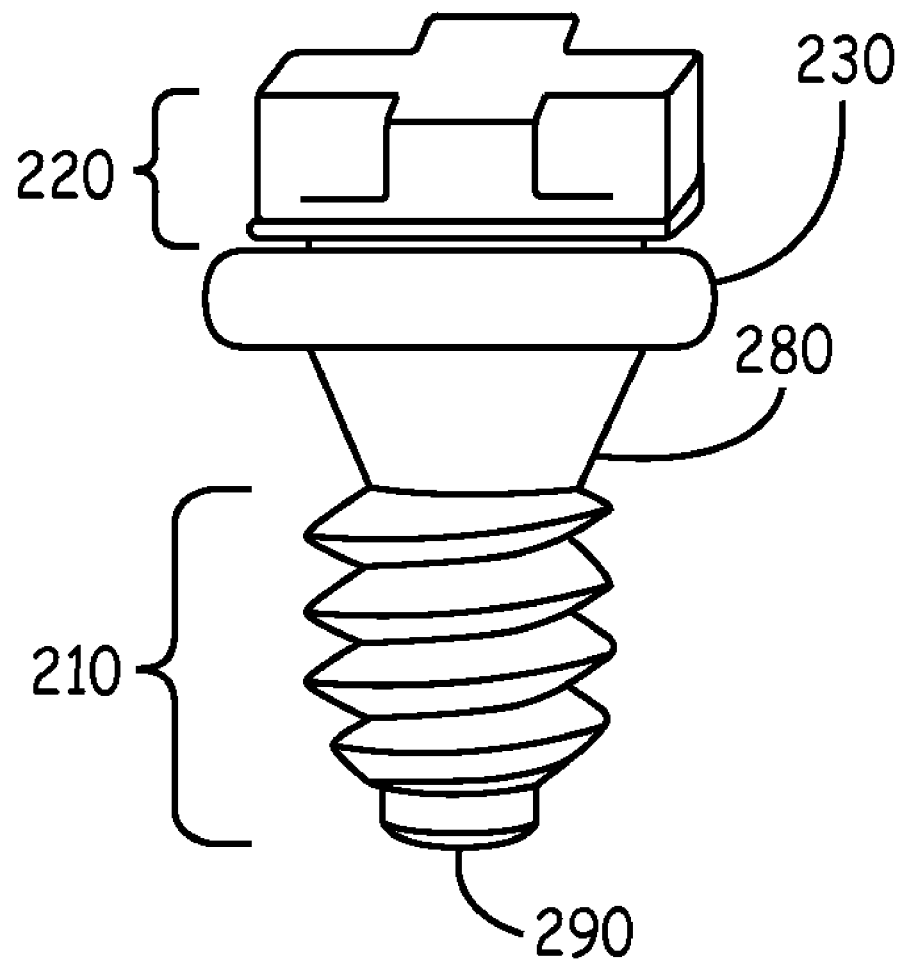
FIG. 10 illustrates a perspective view of yet another alternative embodiment of a setscrew of the present disclosure.

FIG. 10 illustrates a perspective view of yet another embodiment of setscrew 200. In one example, shoulder 280 is tapered towards base 290 of setscrew 200. The degree of taper of shoulder 280 is varied in the range between zero (0) to ninety (90) degrees. In another example, shoulder 280 has a rounded edge.

Figure 11:
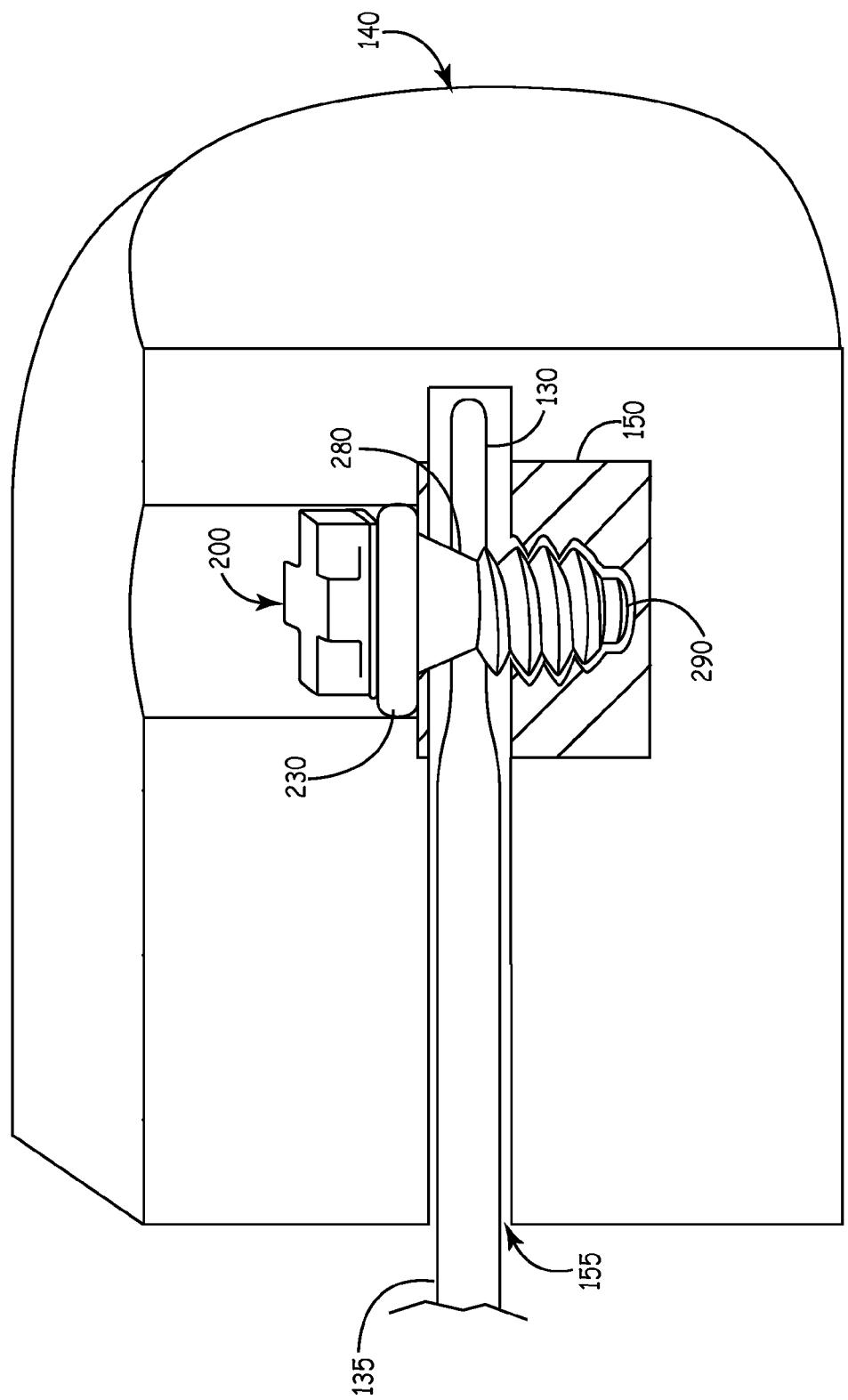
FIG. 11 illustrates a perspective view of an alternative embodiment of a coupling of lead within a header.

With particular attention now to FIG. 11, an alternative embodiment of the coupling of lead 135 within header 140 is illustrated. Setscrew bore 165 is formed within connector block 150 in a substantially vertical direction that is transverse to, and in communication with, the longitudinal axis of lead bore 155. Lead bore 155 is formed in a substantially horizontal direction, relative to the orientation of setscrew bore 165. However, unlike the embodiment of FIG. 2, the central longitudinal axis of setscrew bore 165 is offset from the midpoint of the longitudinal axis of lead bore 155. Thus setscrew 200 engages lead 135 at a location other than tip 290. For example, in the embodiment of FIG. 11, when setscrew 200 is threadedly coupled to the setscrew bore 165, lead 135 is engaged by shoulder 280 of setscrew 200. In one or more embodiments, the angle of the taper of shoulder 280 is preferably selected such that the surface in contact between setscrew 200 with lead 135 is approximately tangent to lead 135. Thus, in some examples, the taper of shoulder 280 is selected to be about thirty (30), forty-five (45) or sixty (60) degrees. It will be appreciated that embodiments where shoulder 280 engages lead 135, the surface area in contact between setscrew 200 and lead 135 is greater than that of FIG. 2 where lead 135 is engaged by base 290 of shank 210 of setscrew 200. Moreover, the offset orientation described above permits setscrew 200 and lead 135 to overlap, relative to one another, while still achieving the desired lead 135 retention functionality.

Figure 12A:
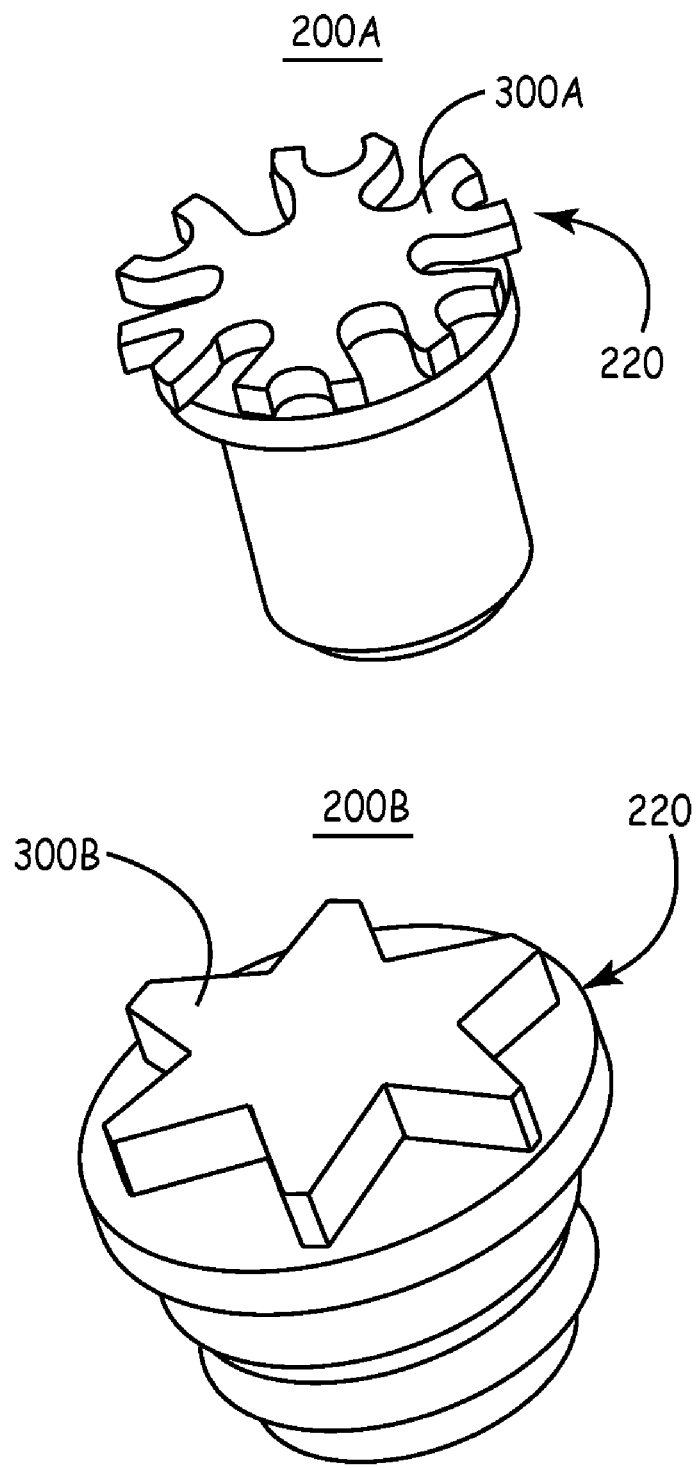
FIGS. 12A-B illustrate alternative embodiments of a setscrew of the present disclosure.
Figure 12B:
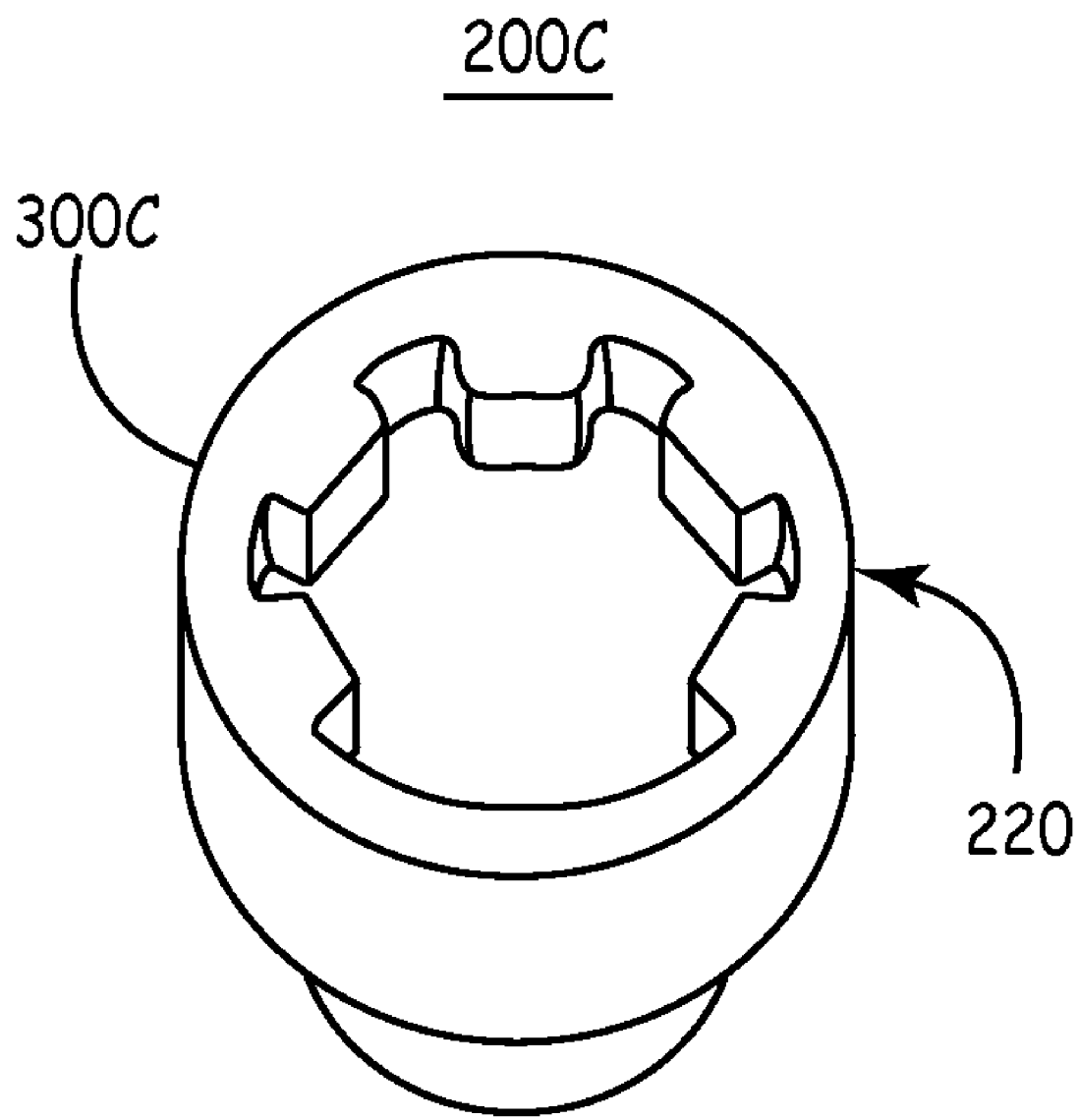

With reference now to FIG. 12A, alternative embodiments of setscrew 200A-B are illustrated. In the exemplary embodiment of setscrew 200A, head portion 220A of core 205 is shown having a star-shaped external drive configuration. The exemplary setscrew 200B shows head portion 220B having a concave-shaped external drive configuration with the concave regions having varying dimensions. It should be noted that the illustrative external drive configurations are merely exemplary and are not intended to be limiting. In alternative embodiments, head portion 220C has an internal drive interface as illustrated in the example of FIG. 12B. Head portion 220C has a hollowed out region, configured with several lobed cutouts, that is integrally formed within head 220. In comparison with an external drive interface, the internal drive interface generally has faces aligned with the thread axis and that face inward in relation to the contact surface of wrench 302.

Figure 13:
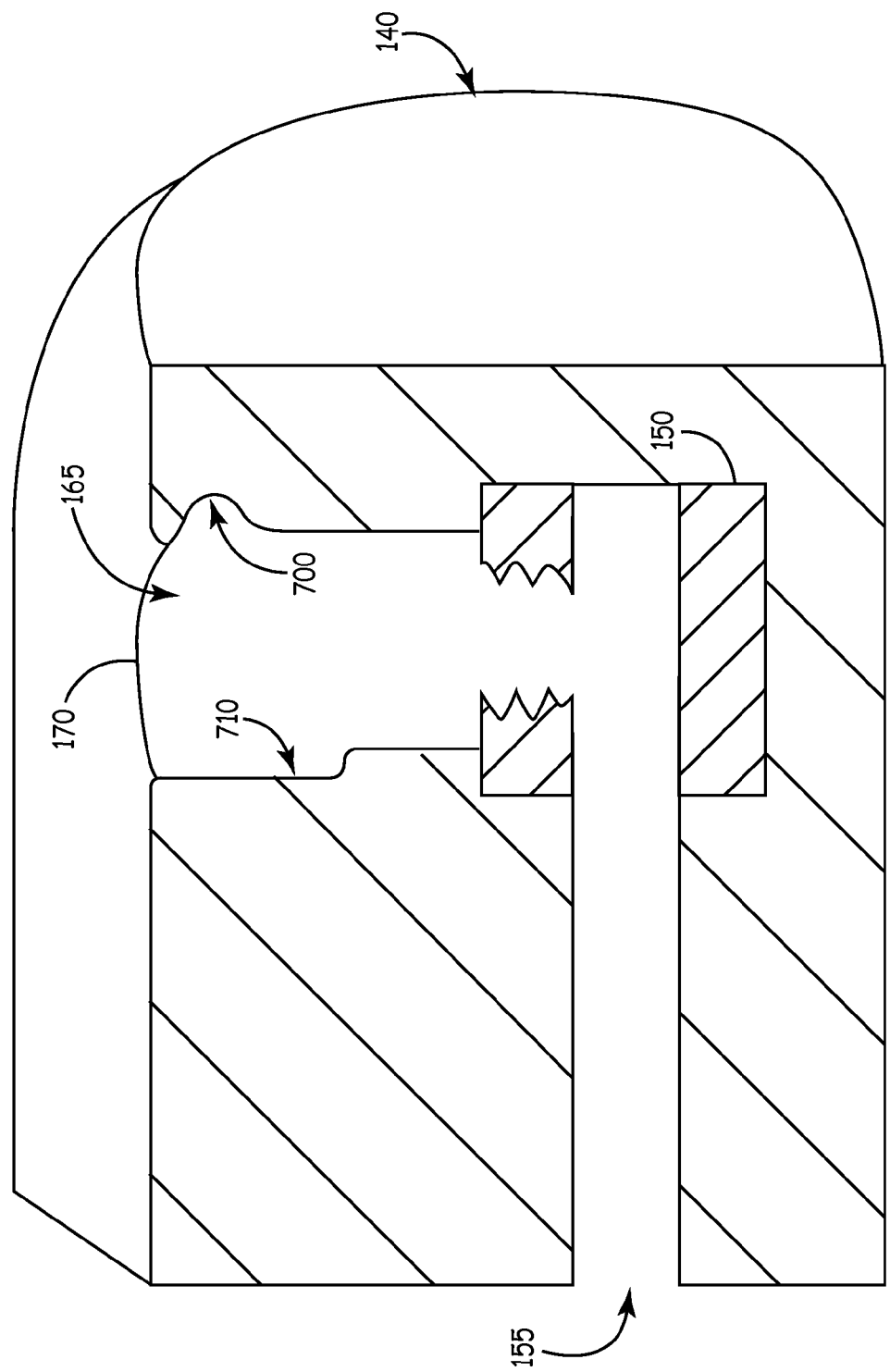
FIG. 13 illustrates a perspective view of a first embodiment of a header of the present disclosure.
Figure 14:
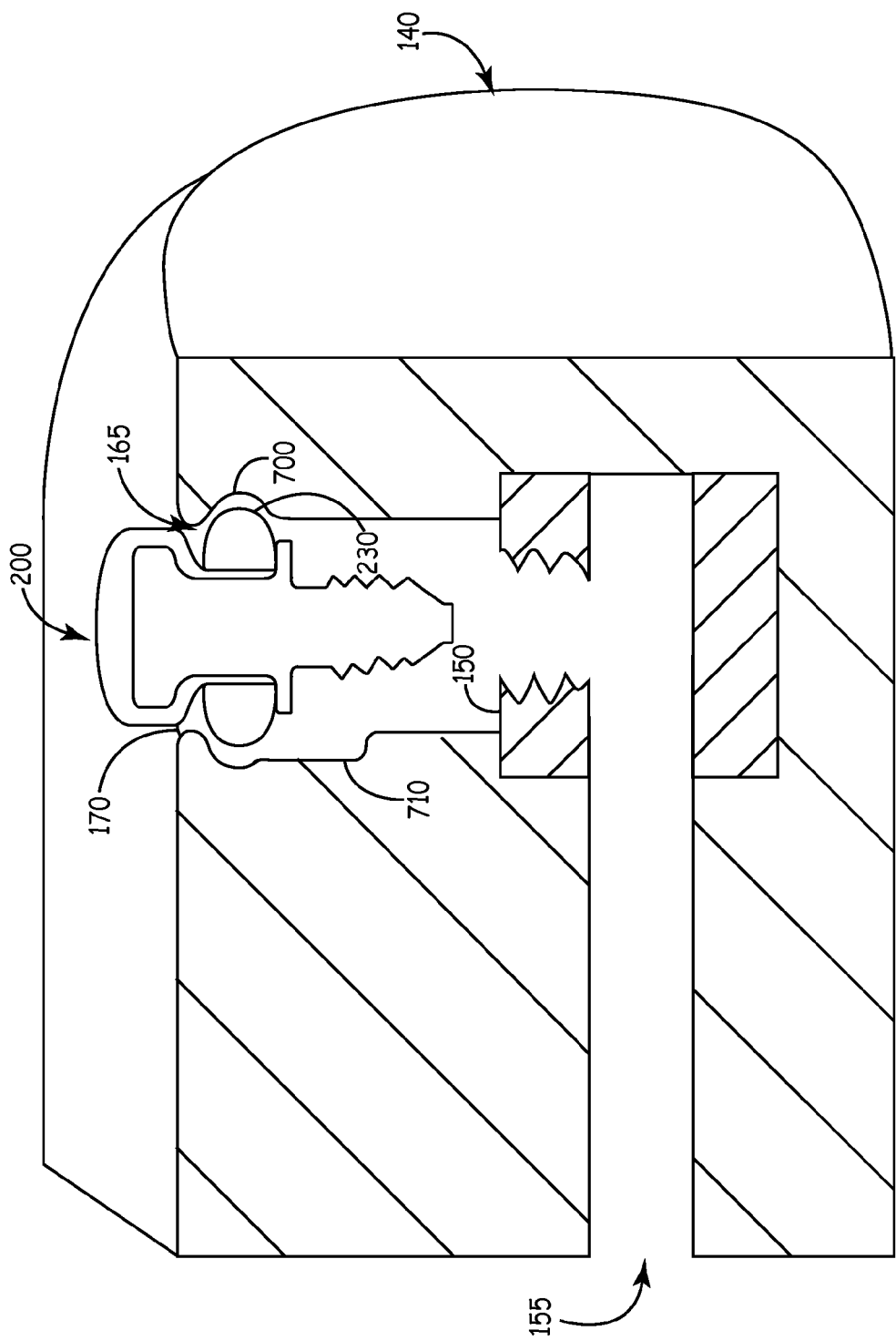
FIG. 14 illustrates a cross-sectional view of the header of FIG. 13, in conjunction with a setscrew of the present disclosure.
Figure 15:
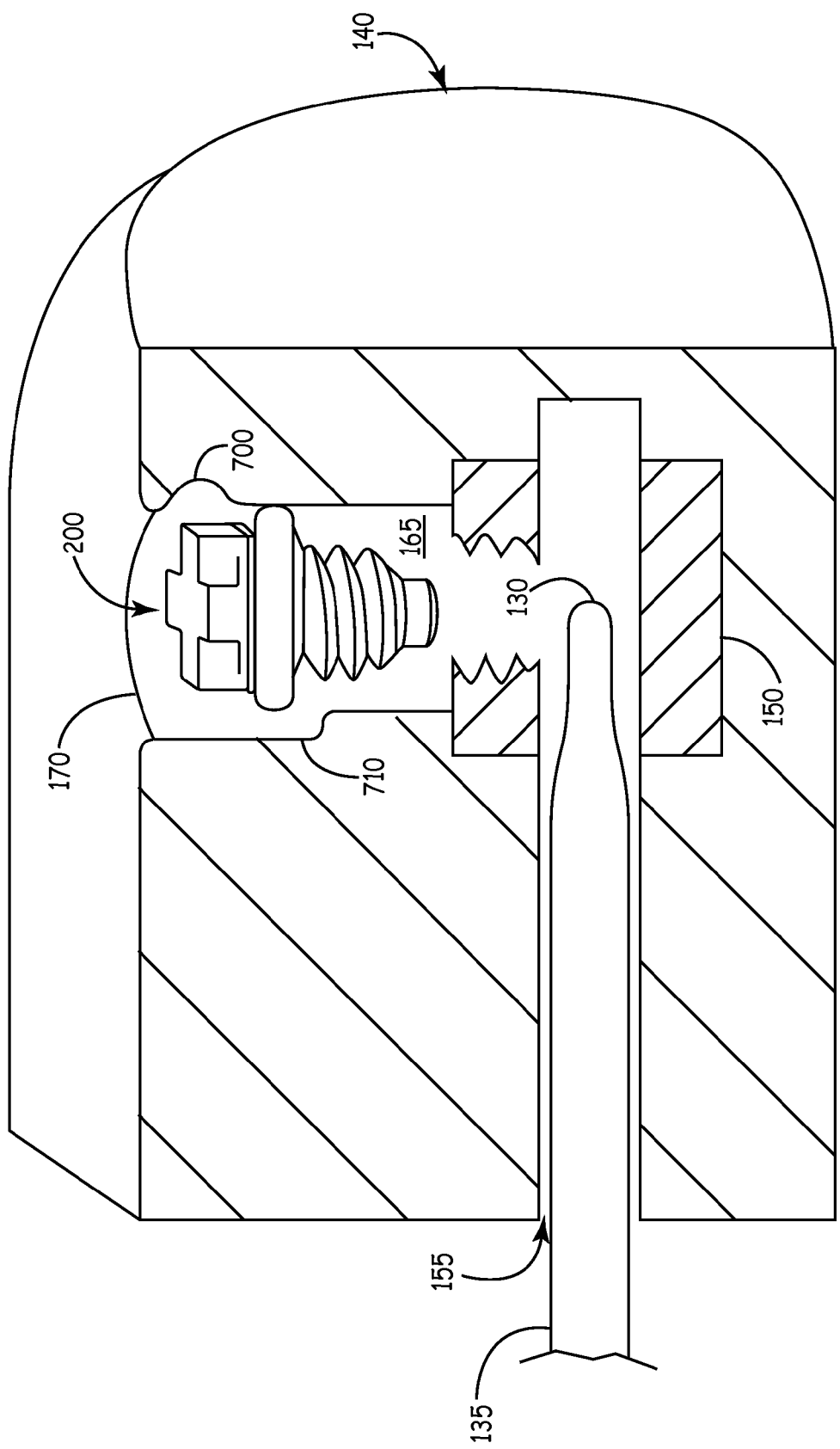
FIG. 15 shows a cross-sectional view of the header of FIG. 14 in connection with a lead.

FIGS. 13-15 illustrate magnified views of an exemplary embodiment of setscrew bore 165 of header 140. As earlier noted, IMD 10 is typically shipped with setscrew 200 already having been inserted in setscrew bore 165. The diameter of setscrew bore 165 is typically sized to be slightly larger than the external diameter of setscrew 200. Thus, the illustrative embodiments of header 140 prevent unintentional falling out of setscrew 200 from setscrew bore 165.

FIG. 13 shows setscrew bore 165 of header 140 having an undercut 700. Undercut 700 is formed within the setscrew bore 165. In some embodiments, undercut 700 is located proximate within the region between an exterior opening 170 and a midpoint of setscrew bore 165. Undercut 700 extends circumferentially at least partially around setscrew bore 165. The structure of undercut 700 resembles a furrow or a groove. Undercut 700 functions to receive a portion of setscrew 200 thereby preventing setscrew 200 from falling out of header 140. Additionally, a venting channel 710 that extends from the proximal opening 170 is formed within setscrew bore 165. In some embodiments, the longitudinal dimension of venting channel 710 is sized such that head 220 will be located within a portion of venting channel 710 when setscrew 200 is disengaged from setscrew bore 165. In one embodiment, venting channel 710 is formed using molding techniques that incorporate venting channel 710 in the formation of setscrew bore 165 within connector block 150. In another example, venting channel 710 is formed by any suitable process that extracts the molding material, such as machining, or carving out to form the desired configuration, or depressing the wall of setscrew bore 165 at the desired location during formation of header 140.

FIG. 14 illustrates a cross-sectional view of header 140 of FIG. 13, in conjunction with setscrew 200. In the illustrative embodiment, undercut 700 receives a portion of setscrew 200 such, for example, as a region having the largest diameter of setscrew 200 or a protrusion of the insulating material. In the exemplary illustration, sealing member 230 has the largest diameter of setscrew 200 and thus is received by undercut 700. Consequently, as setscrew 200 retracts from setscrew bore 165, sealing member 230 is engaged within undercut 700 thereby preventing setscrew 200 from leaving the confines of setscrew bore 165. In alternative implementations, undercut 700 is formed of several partial regions spaced around setscrew bore 165.

Referring to FIG. 15, the insertion of lead 135 into header 140 of FIG. 14 is illustrated. It should be noted that insertion of lead 135 into lead bore 155 will cause displacement of air within lead bore 155 and connector block 150. With reference to FIG. 2 by way of illustration, when setscrew 200 is inserted into setscrew bore 165, sealing member 230 compresses against the walls of setscrew bore 165 thereby sealing the bore 165 and preventing flow of air. Consequently, the air in lead bore 155 causes a piston-like effect when lead 135 is inserted. In other words, the air will oppose insertion of lead 135 thereby encumbering the assembly during an implantation. Turning then to FIG. 15, as lead 135 is inserted into lead bore 155, the air within lead bore 155 is permitted to freely flow between venting channel 710 and sealing member 230. As an illustration, this free movement of air occurs through venting channel 710. Additionally, the completed assembly of IMD 10 is typically sterilized subsequent to insertion of setscrew 200. Venting channel 710 also facilitates the sterilization process of header 140 since the sterilization fluid is permitted to flow through easily. Venting channel 710 is located such that when setscrew 200 is fully unscrewed from the connector block 150, fluids can freely pass through venting channel 710. Yet, when setscrew 200 is fully screwed into the connector block 150, fluids cannot freely pass by the sealing member 230 because the venting channel 710 does not pass through the zone between the location of the sealing member 230 when setscrew 200 is fully screwed into the connector block 150.

Figure 16:
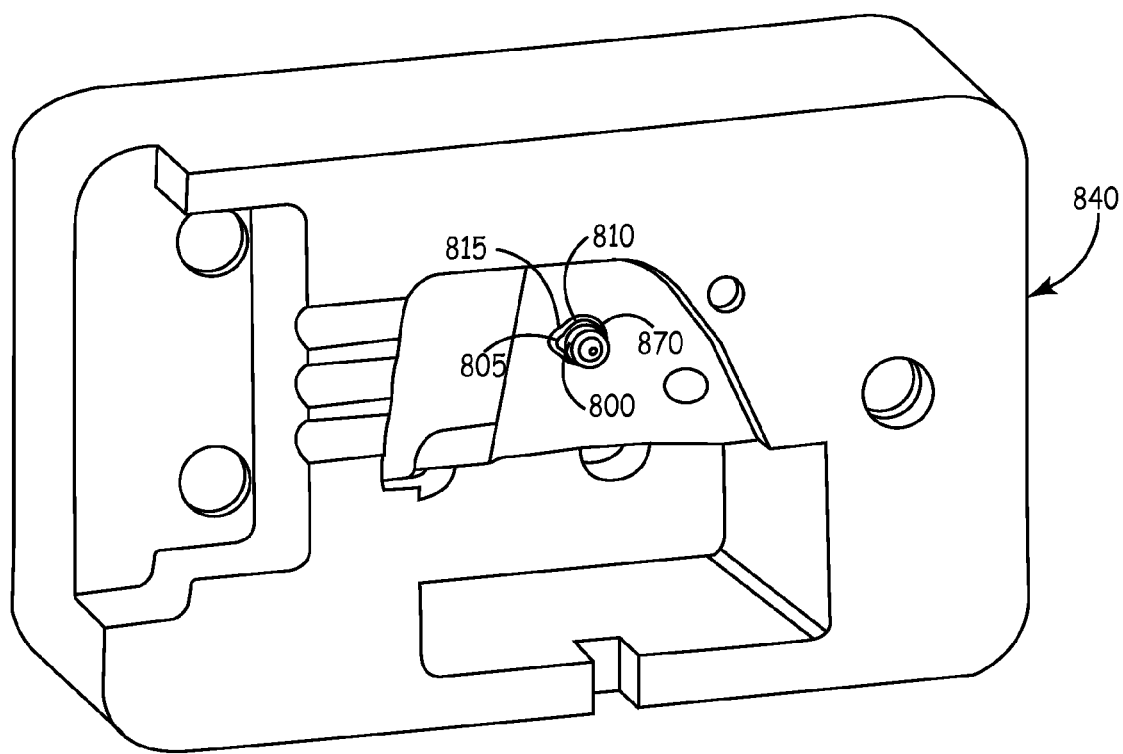
FIGS. 16-17 illustrate an exemplary process for making the header of FIG. 13.
Figure 17:
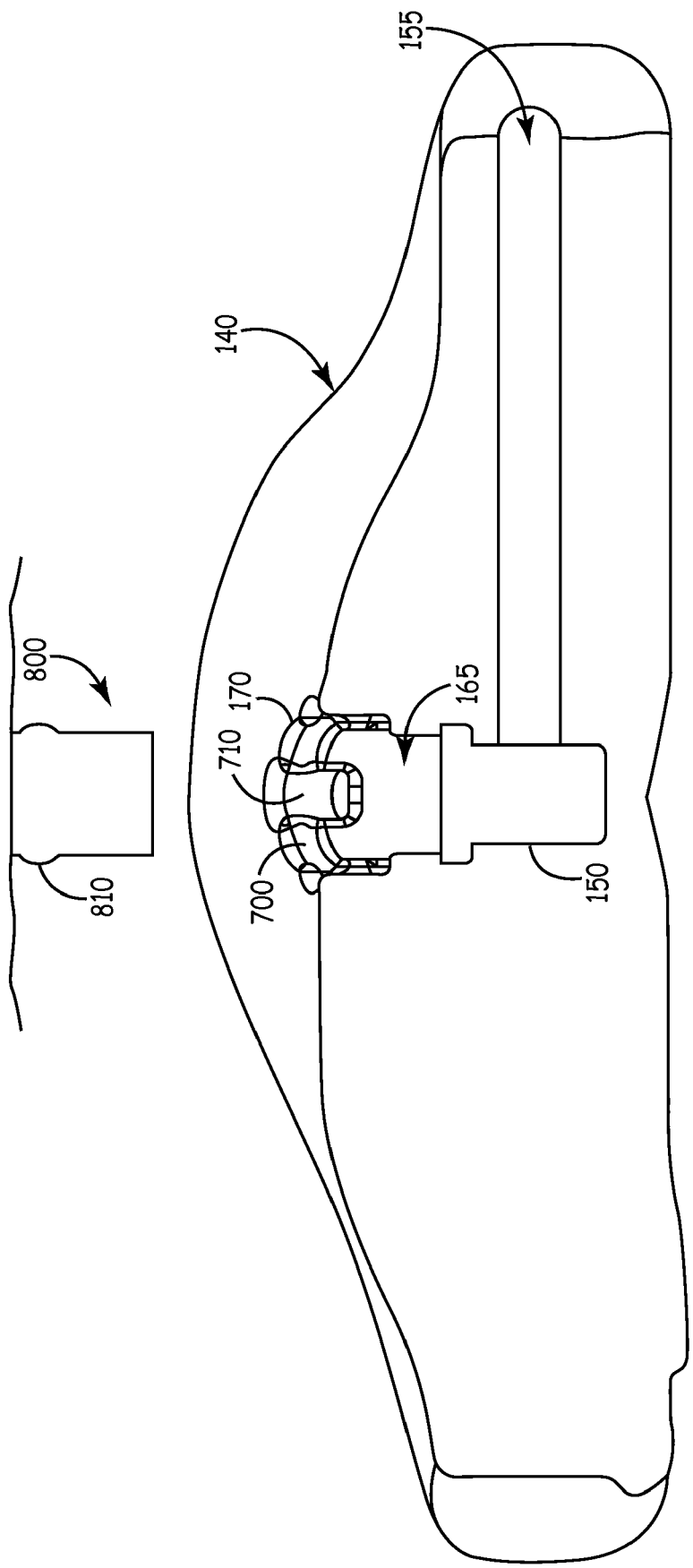

FIGS. 16-17 illustrate an exemplary process for manufacturing setscrew bore 165 having undercut 700 within header 140. It should be noted that the exemplary molding process for molding header 140 typically includes the use of a mold 840 having identical features to those of the desired header 140 that are inverse to those of header 140. The manufacturing process used for the formation of header 140 is any suitable molding process such, for example, as injection molding.

FIG. 16 is a perspective view of a portion of exemplary mold 840 for the formation of header 140. Mold 840 is provided with a setscrew bore-forming pin 800 for the formation of a setscrew bore 165. Setscrew bore-forming pin 800 has a raised rib 810 for the formation of undercut 700. The diameter of raised rib 810 is sized to be larger than the diameter of the setscrew bore-forming pin 800 such that the point of contact between raised rib 810 defines the desired undercut 700. Pin 800 is also provided with an extended longitudinal portion 805 for the formation of venting channel 710. At least one crest 815 is provided along the circumference of a proximal end 870 of pin 800.

A molding process, such as injection molding, is performed to fill mold 840 with a molding material that is shaped into header 140. The material is allowed to cure and subsequently, the formed header 140 is separated from mold 840. In one example, the step of curing includes providing sufficient time for the molded material to settle and cool to a room temperature, or about twenty degrees Celsius. The material used in the molding process is a creep recovering material, or has certain deflection properties such that the material temporarily deforms when stress is exerted upon it but substantially returns to its original form when the stress is withdrawn. In one example, the material is a biocompatible material that has elastic "memory" such as TECOTHANE® thermoplastic polyurethanes.

FIG. 17 illustrates the step of ejection of pin 800 during the separation of mold 840 from the molded header 140. During the ejection, raised rib 810 causes an outward expulsion of the material proximate the raised rib 810. However, crest 815 will facilitate a controlled outward expulsion of the material at exterior opening 170 during the withdrawal motion and prevent rupture. In one example, four crests 815 are provided so that the ejection of pin 800 will cause the material to be separated into quadrants during the expulsion. Subsequent to the ejection of pin 800, the expelled material will substantially re-form back into its pre-expulsion location because of its elastic memory and deflection properties. This re-forming creates undercut 700 at the point of contact with raised rib 810 and venting channel 710 at the location of extended longitudinal portion 805.

In alternative embodiments, a flattening process is additionally utilized to further re-form molded header 140 and/or to create a smooth surface finishing along exterior opening 170 of setscrew bore 165 and the surrounding edge. In one example, the flattening process includes an annealing technique or application of heat to re-shape the material around exterior opening 170. In another example, the flattening process includes the application of a physical force to depress the material back into setscrew bore 165. In alternative embodiments, sealing member 230 is coupled to setscrew bore 165. Sealing member 230 may be coupled using any known bonding technique such, for example, as a silicone adhesive.

Figure 18A:
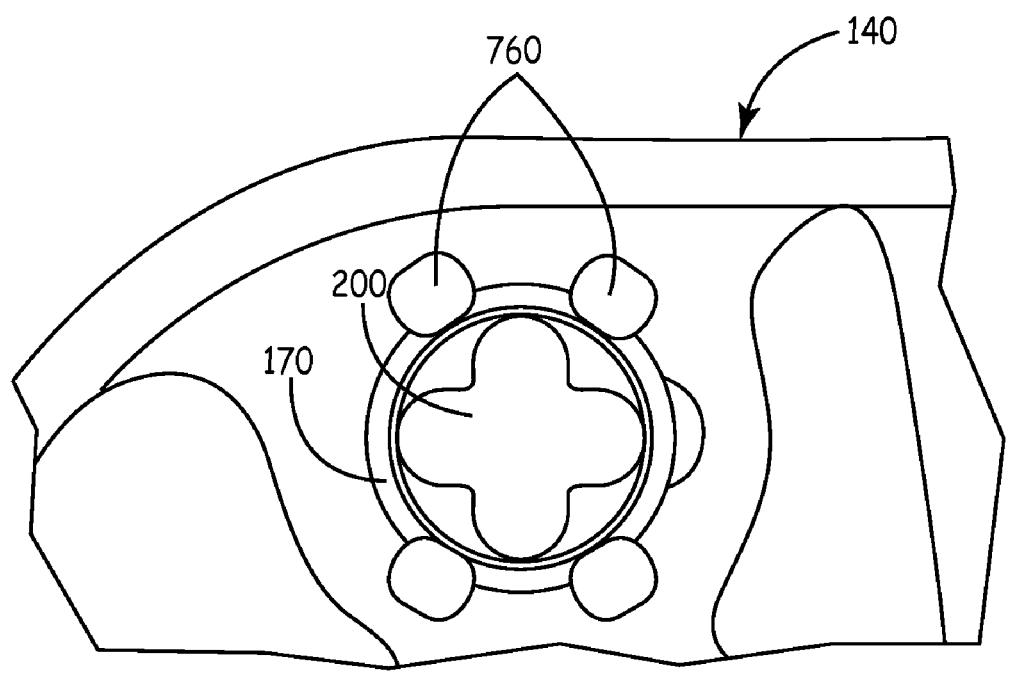
FIG. 18A-B illustrate perspective views of a second embodiment of a header of the present disclosure.
Figure 18B:
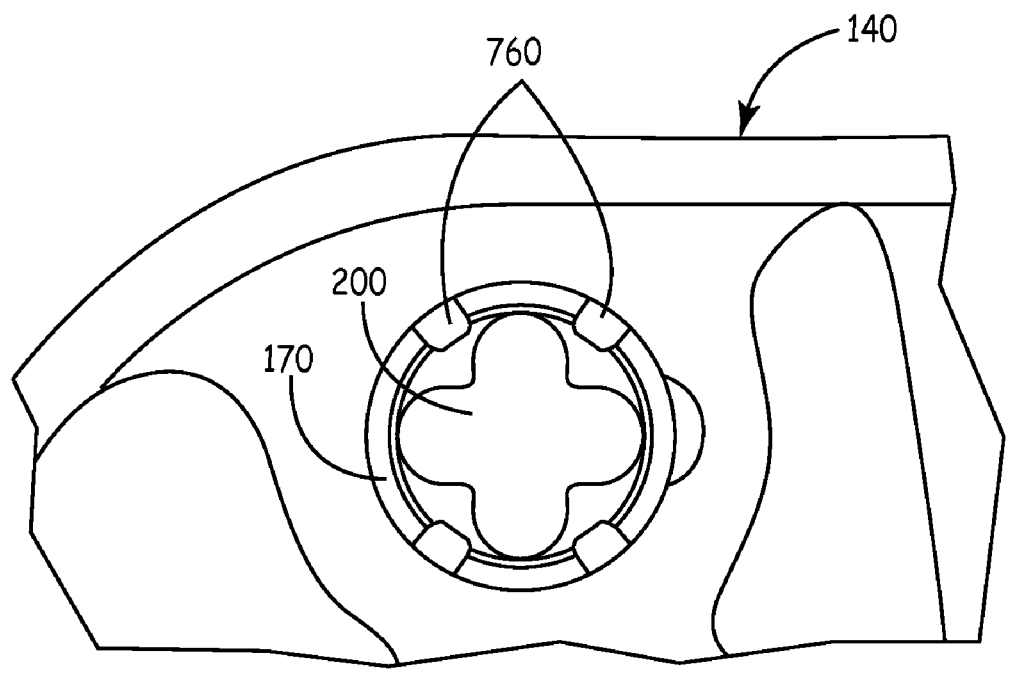

FIGS. 18A-B illustrate an alternative embodiment of header 140 having one or more protruding members 760. In the exemplary embodiment, protruding members 760 are posts molded as part of header 140 to extend adjacent to exterior opening 170. In an example, the protruding members 760 are molded from the same material as the header 140. As illustrated in FIG. 18B, upon insertion of setscrew 200, the protruding members 760 are reflowed downward toward setscrew bore 165 using any suitable reflow process such as ultrasonic welding so as to protrude over exterior opening 170 thereby preventing setscrew 200 from falling out.

Figure 19:
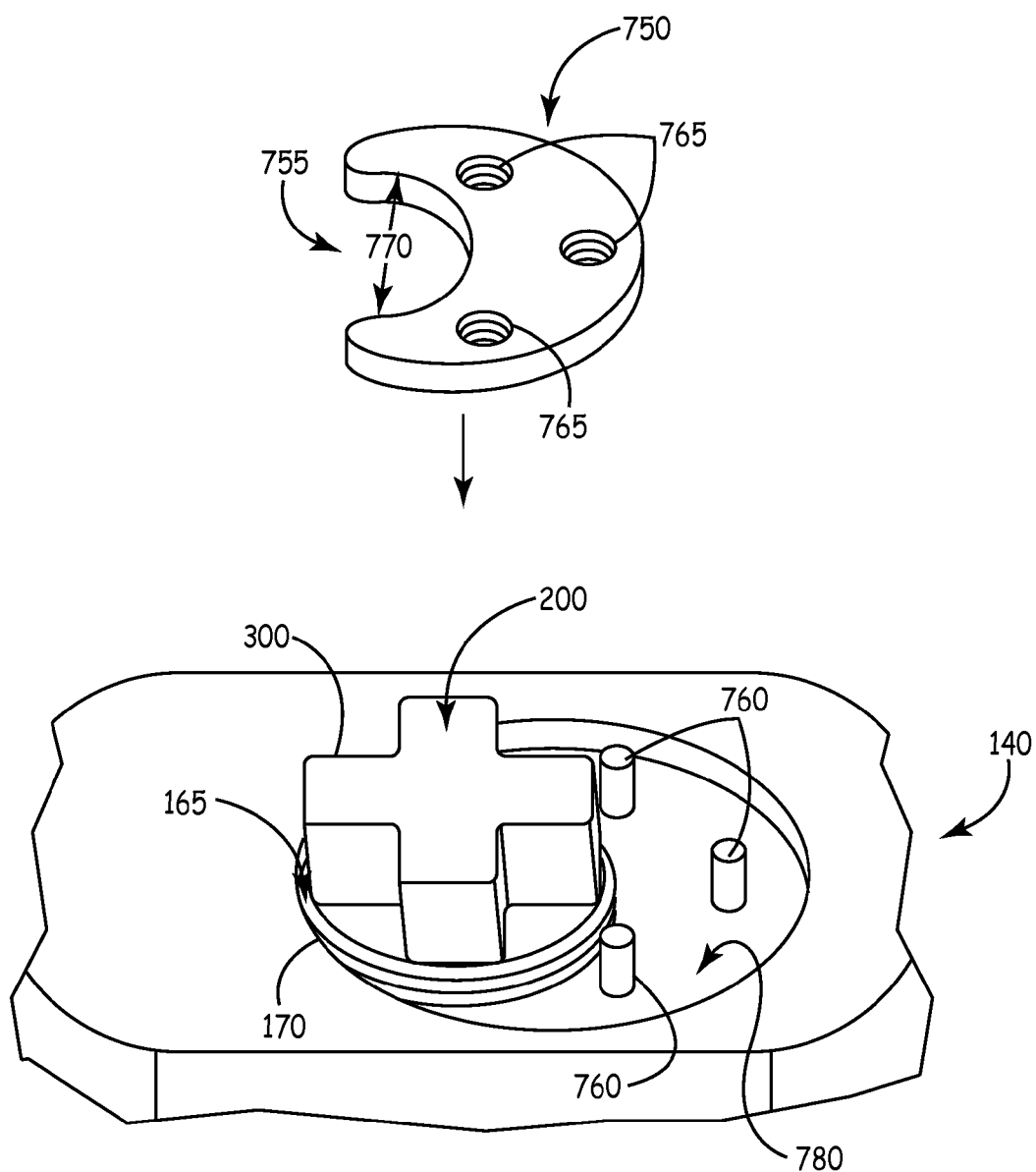
FIG. 19 illustrates a perspective view of a third embodiment of a header of the present disclosure.

FIG. 19 illustrates a capture mechanism 750 extending over exterior opening 170 of setscrew bore 165. In some embodiments, capture mechanism 750 has a radial opening 755 having a diameter that is less than the diameter of setscrew 200. Thus, when setscrew 200 is retracted from setscrew bore 165, capture mechanism 750 prevents setscrew 200 from falling out of setscrew bore 165. In one embodiment, capture mechanism 750 is a rigid thin plate that is formed such that it defines a trough-shaped opening 755. The exemplary opening 755 is sized to enable insertion of torque wrench 302 for tightening or loosening setscrew 200. In one embodiment, channel 755 on capture mechanism 750 is aligned with a vertical axis of setscrew 200 to provide a continual line of vision to lead 135. Capture mechanism 750 is created from a bio-compatible rigid material such, for example, as TECOTHANE® thermoplastic polyurethanes or titanium. Capture mechanism 750 is bonded to header 140 for example, at region 780, proximate to exterior opening 170. In one example, capture mechanism 750 is bonded through the coupling of posts 760 to correspondingly sized holes 765 by a reflow process. In another embodiment, the capture mechanism 750 is a flat washer with a hole in approximately the middle that is large enough to allow the torque wrench 302 to pass but smaller than the maximum diameter of the setscrew to prevent the setscrew from falling out of the sealing bore. In one embodiment, capture mechanism 750 is formed as part of the header 140 by constructing a correspondingly shaped mold.

The specific shape and size of capture mechanism 750 is predicated on keeping setscrew 200 from falling out while in its disengaged position. The shape and size of radial dimension 770 of opening 755 is controlled by various factors, for example, the assembly requirements including the size and shape of the torque wrench 302, the shape of the tool interface 300 and/or the coupling technique. By way of example which is not intended to be limiting, alternative embodiments of capture mechanism 750 have radial dimension 770 formed to define a v-shape, or a u-shape. Additionally, the variation of radial dimension 770 facilitates the reduction of the spacing between multiple setscrew bores 165. Thus, the variation of radial dimension 770 also enables reduction in size of header 140.

In the foregoing detailed description, the present disclosure has been described in considerable detail in order to comply with the patent statutes and to provide those skilled in the art with specific implementations that facilitate the understanding of the novel principles of the disclosure. However, it is to be understood that the principles of the present disclosure can be carried out by specifically different equipment and devices and that various modifications, both as to the equipment and operating procedures, can be accomplished without departing from the scope of the disclosure as set forth in the appended claims.

What is claimed is:

1. An implantable medical device (IMD) header assembly, comprising:
    a header;
    a connector block disposed within the header, the connector block including a lead bore and a setscrew bore, the lead bore having a transverse orientation relative to and being in communication with setscrew bore; and
    a capture mechanism disposed within a sidewall of the setscrew bore, wherein the capture mechanism comprises an undercut formed to define a C-shaped furrow that is located proximate to an exterior opening of the setscrew bore.

2. The IMD header of claim 1, wherein the undercut extends at least partially within the circumference of the setscrew bore.

3. The IMD header of claim 1, further comprising a setscrew having:
    a head portion integrally formed with a shank portion, the head portion having an engagement segment configured for application of torque, wherein the shank portion has a threaded outer surface configured for coupling to a mating threaded bore of the IMD;

a necked region disposed between the head portion and the shank portion; and an insulating coating substantially encapsulating the head portion to electrically isolate the head portion, wherein the insulating coating is placed in substantial compression when the torque is applied to the head portion.

4. The IMD header of claim 1, further comprising a sealing member disposed within the setscrew bore.

* * * * *